US008450482B2

United States Patent
Boardman et al.

(10) Patent No.: US 8,450,482 B2
(45) Date of Patent: May 28, 2013

(54) PROCESS FOR THE PREPARATION OF 4-(3-CHLORO-2-FLUOROANILINO)-7-METHOXY-6-([1-(N-METHYL-CARBAMOYMETHYL)PIPERIDIN-4-YL]OXY)QUINAZOLINE

(75) Inventors: Kay Alison Boardman, Cheshire (GB); Oliver Robert Cunningham, Cheshire (GB); William Robert Fraser Goundry, Cheshire (GB); David Dermot Patrick Laffan, Cheshire (GB)

(73) Assignee: Astrazeneca AB, Sodertalje (SE)

( * ) Notice: Subject to any disclaimer, the term of this patent is extended or adjusted under 35 U.S.C. 154(b) by 0 days.

(21) Appl. No.: 13/264,217

(22) PCT Filed: Apr. 22, 2010

(86) PCT No.: PCT/GB2010/050653
§ 371 (c)(1),
(2), (4) Date: Dec. 14, 2011

(87) PCT Pub. No.: WO2010/122340
PCT Pub. Date: Oct. 28, 2010

(65) Prior Publication Data
US 2012/0108814 A1    May 3, 2012

Related U.S. Application Data

(60) Provisional application No. 61/171,994, filed on Apr. 23, 2009.

(51) Int. Cl.
  *C07D 239/72*    (2006.01)

(52) U.S. Cl.
  USPC .......................................... 544/293; 544/245

(58) Field of Classification Search
  USPC ................................... 544/245, 293
  See application file for complete search history.

(56) References Cited

U.S. PATENT DOCUMENTS

| 6,924,285 | B2 | 8/2005 | Himmelsbach et al. |
| 7,119,084 | B2 | 10/2006 | Himmelsbach et al. |
| 8,088,782 | B2 * | 1/2012 | Dobson ............. 514/266.4 |

FOREIGN PATENT DOCUMENTS

| WO | 03/082831 A1 | 10/2003 |
| WO | 2005/023783 A1 | 3/2005 |
| WO | 2005/028469 A1 | 3/2005 |
| WO | 2005/115145 A2 | 12/2005 |
| WO | 2009/138779 A1 | 11/2009 |
| WO | 2009/138781 A1 | 11/2009 |

OTHER PUBLICATIONS

Database Casreact Chemical Abstracts Services 2007,XP002603411, Database accession No. 148:331709 abstract pp. 4-8.

* cited by examiner

*Primary Examiner* — Golam M M Shameem
(74) *Attorney, Agent, or Firm* — Astrazeneca AB

(57) ABSTRACT

Processes for the preparation of 4-(3-chloro-2-fluoroanilino)-7-methoxy-6-{[1-(N-methylcarbamoylmethyl)piperidin-4-yl]oxy}quinazoline, salts thereof, and the intermediates used in the process are described.

8 Claims, 5 Drawing Sheets

Figure 2 - - Powder X-ray diffraction pattern of Compound (I) as a 2-methyltetrahydrofuran solvate Figure 3 - Powder X-ray diffraction pattern of Compound (I) as a hydrate Figure 4 - Powder X-ray diffraction pattern of Compound (I) as an isopropanol solvate

PROCESS FOR THE PREPARATION OF 4-(3-CHLORO-2-FLUOROANILINO)-7-METHOXY-6-([1-(N-METHYL-CARBAMOYMETHYL)PIPERIDIN-4-YL]OXY)QUINAZOLINE

CROSS-REFERENCE TO RELATED APPLICATIONS

This application is a U.S. National Stage under 35 U.S.C. §371 of International Application No. PCT/GB2010/050653 (filed Apr. 22, 2010) which claims priority under 35 U.S.C. §119 (e) to U.S. Provisional Application No. 61/171,994 (filed Apr. 23, 2009).

The present invention relates to processes for the preparation of 4-(3-chloro-2-fluoroanilino)-7-methoxy-6-{[1-(N-methylcarbamethoylmyl)piperidin-4-yl]oxy}quinazoline or a to salt thereof; hereafter "compound (I)", and to intermediates used in the preparation of compound (I).

BACKGROUND

Compound (I) is disclosed in International Patent Application Publication number WO2005/028469 as Example 1 therein and is of the structure:

Compound (I)

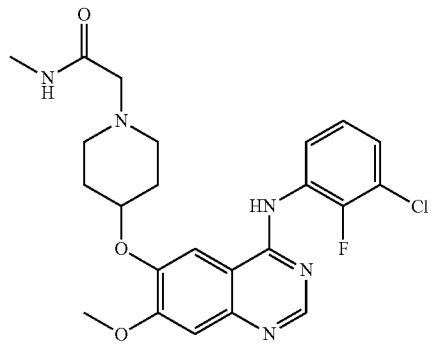

Compound (I) is an erbB receptor tyrosine kinase inhibitor, in particular compound (I) is a potent inhibitor of EGFR and erbB2 receptor tyrosine kinases. Compound (I) also inhibits erbB3 mediated signalling through the inhibition of phosphorylation of erbB3 following ligand stimulated EGFR/erbB3 and/or erbB2/erbB3 heterodimerisation. Compound (I) is expected to be useful in the treatment of hyperproliferative disorders such as cancer.

WO 03/082831 discloses the preparation of various 4-(3-chloro-2-fluoroanilino)quinazolines. However, compound (I) is not disclosed therein.

WO2005/028469 discloses as Example 1 therein the preparation of compound (I) as follows:

2-Chloro-N-methylacetamide (32 mg, 0.3 mmol) was added to a mixture of 4-(3-chloro-2-fluoroanilino)-7-methoxy-6-[(piperidin-4-yl)oxy]quinazoline (120 mg, 0.3 mmol), potassium iodide (16 mg, 0.1 mmol), and potassium carbonate (50 mg, 0.36 mmol) in acetonitrile (5 ml). The mixture was heated at reflux for one hour. After evaporation of the solvents under vacuum, the residue was taken up in dichloromethane. The organic solution was washed with water and brine, dried over magnesium sulfate. After evaporation of the solvents under vacuum, the residue was purified by chromatography on silica gel (eluant: 1% to 2% 7 N methanolic ammonia in dichloromethane) to give compound (I).

SUMMARY

We have found an alternative process for the preparation of compound (I), which provides compound (I) with a reduced number of process steps in high yield and with minimal impurities. The process is therefore suitable for use in the large-scale manufacture of compound (I).

On embodiment provide a process for the preparation of 4-(3-chloro-2-fluoroanilino)-7-methoxy-6-{[1-(N-methyl-carbamoylmethyl)piperidin-4-yl]oxy}quinazoline or a salt thereof comprising:

(a) reacting a compound of formula (II):

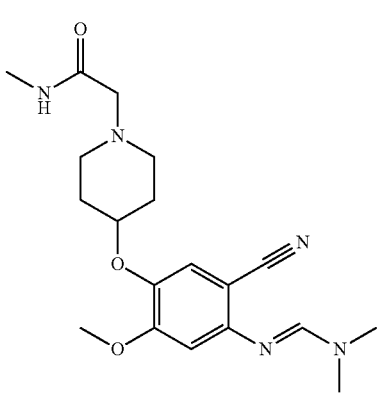

II with 3-chloro-2-fluoroaniline in the presence or a suitable acid; or (b) reacting a compound of formula (III):

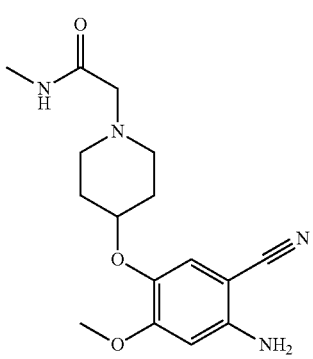

III with a compound of formula (XI) or formula (XII):

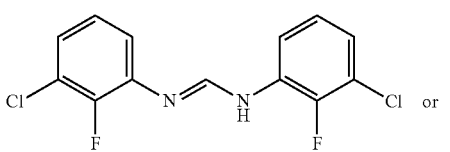

XI

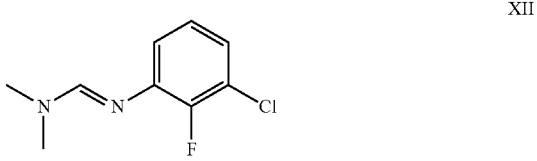

XII in the presence of a suitable acid.

DETAILED DESCRIPTION

On embodiment provide a process for the preparation of 4-(3-chloro-2-fluoroanilino)-7-methoxy-6-{[1-(N-methyl-carbamoylmethyl)piperidin-4-yl]oxy}quinazoline or a salt thereof comprising:

(a) reacting a compound of formula (II):

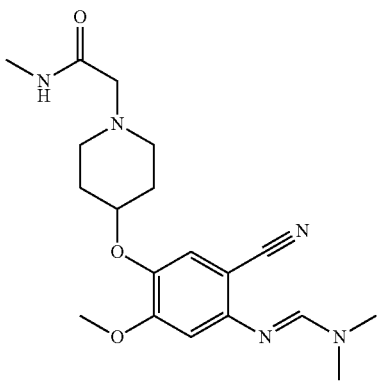

II with 3-chloro-2-fluoroaniline in the presence of a suitable acid.

The reaction is suitably carried out in the presence of a suitable acid, such as one or more acids selected from acetic, butanedioic, propanoic, succinic, fumaric and citric acid, or a mixture thereof. In one embodiment of the invention the acid is acetic acid.

The reaction is suitably carried out in the presence of an inert solvent, for example cyclohexane, an aromatic hydrocarbon solvent such as toluene, methoxybenzene or xylene; a nitrile solvent such as acetonitrile; an ether such as 2-methyltetrahydrofuran; or an ester such as isopropyl acetate. In one embodiment the solvent is selected from toluene, cyclohexane, methoxybenzene, xylene, acetonitrile, 2-methyltetrahydrofuran and isopropyl acetate. In another embodiment the solvent is selected from toluene, cyclohexane, methoxybenzene and xylene. In a further embodiment the solvent is methoxybenzene.

The reaction is suitably carried out at elevated temperature, for example from about 80 to about 120° C., for example at about 90 to 120° C., and suitably at about 90° C.

Suitably an equimolar or molar excess of the 3-chloro-2-fluoroaniline is used relative to the compound of formula (II). For example, the molar ratio of 3-chloro-2-fluoroaniline to compound of formula (II) from about 1:1 to about 1:2, suitably about 1:1.

In any embodiment, compound (I) can be isolated using conventional methods. For example, compound (I) may be extracted into water and crystallised from solution as described in the Examples. If necessary, crystallisation of compound (I) from solution can be initiated by seeding the solution with crystals of compound (I). The resulting solid can then be collected using conventional methods for example by filtration and drying of the compound (I).

According to a further aspect of the present invention there is provided a process for the preparation of a compound of the formula (II) comprising reacting a compound of the formula (III):

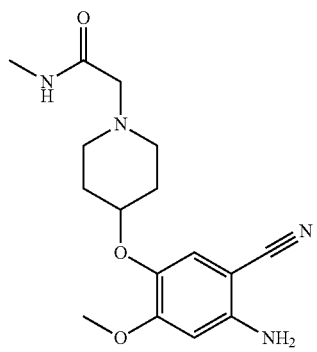

III with N,N-dimethylformamide dimethyl acetal.

The reaction is suitably carried out under acidic conditions. For example the reaction is suitably carried out in the presence of acetic acid.

The reaction is conveniently carried out in the presence of a suitable solvent such as an ether, for example, 2-methyltetrahydrofuran or an aromatic hydrocarbon such as toluene. The reaction is suitably performed at an elevated temperature, for example at about 70 to 105° C., suitably about 76° C.

In another embodiment, compound (I) can be made directly from the compound of Formula (III) by reacting the compound of formula (III) with N,N'-bis(3-chloro-2-fluorophenyl)imidoformamide (compound (XI)). The reaction is suitably carried out under acidic conditions. The reaction is suitably carried out in the presence of a suitable acid, such as one or more acids selected from acetic, butanedioic, propanoic, succinic, fumaric and citric acid, or a mixture thereof. In one embodiment of the invention the acid is fumaric acid.

The reaction is conveniently carried out in the presence of a suitable solvent such as an ether, for example, 2-methyltetrahydrofuran. The reaction is suitably performed at an elevated temperature, for example at about 70 to 105° C., suitably about 90° C.

In another embodiment, compound (I) can be made directly from the compound of Formula (III) by reacting the compound of formula (III) with N'-(3-chloro-2-fluoro-phenyl)-N,N-dimethyl-formamidine (compound (XII)). The reaction is suitably carried out under acidic conditions. The reaction is suitably carried out in the presence of a suitable acid, such as one or more acids selected from acetic, butanedioic, propanoic, succinic, fumaric and citric acid, or a mixture thereof. In one embodiment of the invention the acid is fumaric acid.

The compound of the formula (III) may be prepared by a process comprising the reduction of a compound of the formula (IV):

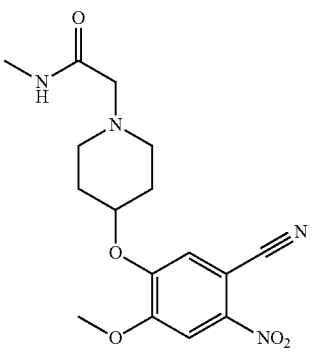

IV

Suitable reduction reactions for reducing nitro groups to amines are well known. For example, the compound of formula (IV) may be reduced by reduction in the presence of a suitable reducing agent such as sodium dithionite. This reaction is suitably carried out in the presence of an aqueous solvent, for example aqueous methanol. The reaction is conveniently performed at elevated temperature for example 40 to 60° C.

Alternatively, reduction of the compound of formula (IV) may be effected by hydrogenation, for example by catalytic hydrogenation with using a suitable catalyst such as a palladium on carbon catalyst, for example a 10% palladium on carbon catalyst, or a platinum/vanadium catalyst, for example 1% platinum+2% vanadium catalyst on carbon. The hydrogenation is conveniently carried out in a suitable solvent such as methanol or acetonitrile. In other embodiments, alternative solvents can also be used, such as methanol, isopropanol or a mixture of methanol:isopropanol in a 1:1 ratio.

The compound of the formula (IV) may be prepared by a process comprising the nitration of a compound of the formula (V):

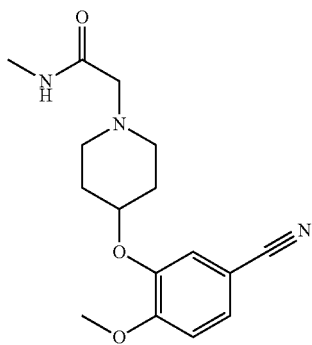

V

The nitration of the compound of the formula (V) may be effected using well known methods for the nitration of aromatic rings, for example by treating the compound of the formula (V) with nitric acid in the presence of sulfuric acid using well known conditions for such reactions and as illustrated in the Examples herein.

The compound of Formula (V) may be prepared by a process comprising the reaction of a compound of the formula (VI):

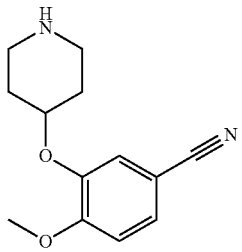

VI with a compound of the formula (VII):

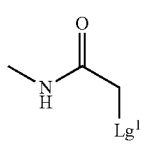

VII wherein $Lg^1$ is a suitable leaving group.

Suitable leaving groups represented by $Lg^1$ include, for example, halogeno, such as is chloro.

The reaction is suitably carried out in the presence of a suitable base such as a carbonate, an organic amine or an alkoxide. Particular bases include, for example, potassium carbonate or triethanolamine.

The reaction is conveniently carried out in the presence of an inert solvent such as acetonitrile or an alcohol such as ethanol. The reaction is suitably performed at an elevated temperature, conveniently the reflux temperature of the solvent.

The compound of formula (VI) may be prepared by, for example, as illustrated in Reaction Scheme 1:

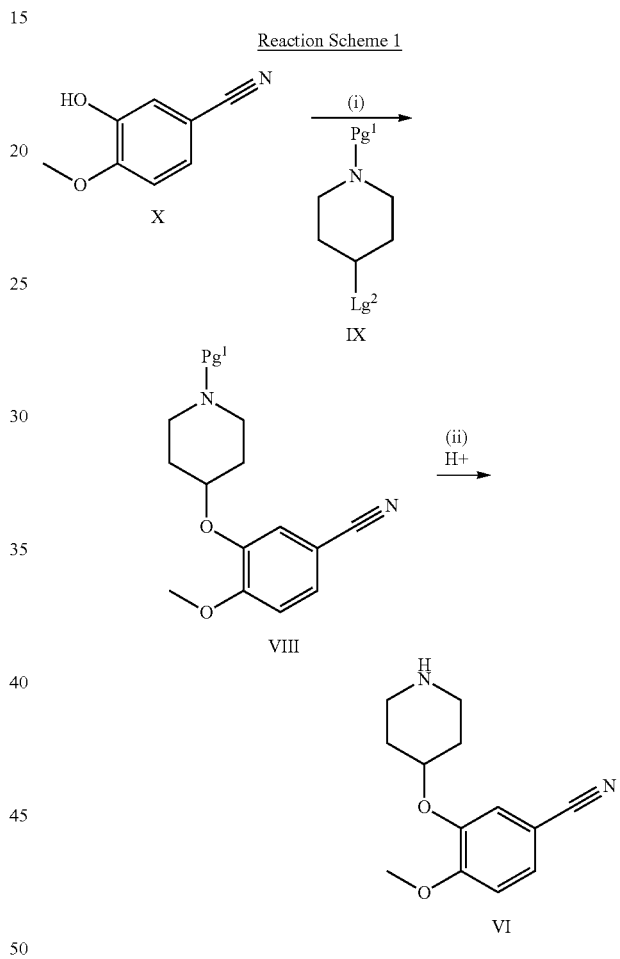

Reaction Scheme 1

Notes on Reaction Scheme 1:

Step (i): $Lg^2$ is a suitable leaving group, for example, a halogeno, alkanesulfonyloxy or arylsulfonyloxy group, for example a chloro, bromo, methanesulfonyloxy, 4-nitrobenzenesulfonyloxy or toluene-4-sulfonyloxy group. Suitably $Lg^2$ is a methanesulfonyloxy, 4-nitrobenzenesulfonyloxy or toluene-4-sulfonyloxy group, for example $Lg^2$ is methanesulfonyloxy.

$Pg^1$ is a suitable amine protecting group. Such groups are well known, for example as described in one of the many general texts on the subject, such as, 'Protective Groups in Organic Synthesis' by Theodora Green (publisher: John Wiley & Sons). Examples of amino protecting groups include an acyl group, for example an alkanoyl group such as acetyl, an alkoxycarbonyl group, for example a methoxycarbonyl, ethoxycarbonyl or tert-butoxycarbonyl group, an arylmethoxycarbonyl group, for example benzyloxycarbonyl, or an aroyl group, for example benzoyl. A particular example of Pg¹ is tert-butoxycarbonyl.

The reaction is suitably carried out in the presence of a base, for example a carbonate such as potassium carbonate. The reaction is conveniently carried out in the presence of a suitable inert solvent, for example an alcohol such as isopropanol. The reaction is suitably carried out at elevated temperature, conveniently at the reflux temperature of the solvent.

Step (ii): The protecting group Pg¹ is removed using conventional methods. For example when Pg¹ is tert-butoxycarbonyl it may be removed by treatment with a suitable acid as hydrochloric, sulfuric or phosphoric acid or trifluoroacetic acid.

In another embodiment, compound (I) can be made directly from the compound of formula (III) by reacting the compound of formula (III) with a compound of formula (XI):

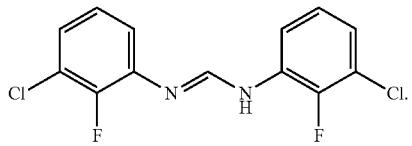

XI

The compound of formula (XI) is also referred to as N,N'-bis(3-chloro-2-fluorophenyl)imidoformamide. The compound of formula (XI) is also referred to as N,N'-bis(3-chloro-2-fluorophenyl)imidoformamide. In another embodiment, compound (I) can be made directly from the compound of formula (III) by reacting the compound of formula (III) with a compound of formula (XII):

XII

The compound of formula (XII) is referred to as N'-(3-chloro-2-fluoro-phenyl)-N,N-dimethyl-formamidine. Either of these reactions are suitably carried out under acidic conditions. For example the reaction is suitably carried out in the presence of acetic acid, butanedioic acid, fumaric acid or propanoic acid.

The reaction is conveniently carried out in the presence of a suitable solvent such as an ether, for example, 2-methyltetrahydrofuran, or an alcohol, for example ethanol or tert-butyl alcohol. The reaction is suitably performed at an elevated temperature, for example at about 70 to 105° C. In some embodiments, the reaction can be carried out at about 80° C. or 90° C.

The compound of formula (XI) can be made by reacting 3-chloro-2-fluoroaniline with ethyl orthoformate. The reaction is suitably carried out under acidic conditions. For example the reaction is suitably carried out in the presence of acetic acid.

The reaction is conveniently carried out in the presence of a suitable solvent such as cyclohexane. The reaction is suitably performed at an elevated temperature, for example at about 40 to 60° C., suitably about 50° C.

Accordingly, compound (I) can be made from the compound of formula (III) through any of the routes described above.

According to another aspect of the invention there is provided a process for the preparation of compound (I), or a pharmaceutically acceptable salt thereof, comprising the steps:

2a) reacting the compound of the formula (II) with 3-chloro-2-fluoroaniline in the presence of a suitable acid; and
1) isolating compound (I).

Suitable conditions for steps 1 to 2 are as hereinbefore defined.

In a further aspect, the process described above can further include the step of:

3a) reacting a compound of the formula (III) as hereinbefore defined with N,N-dimethylformamide dimethyl acetal to give a compound of the formula (II) as hereinbefore defined;

According to another aspect of the invention there is provided a process for the preparation of compound (I), or a pharmaceutically acceptable salt thereof, comprising the steps:

2b) reacting a compound of the formula (III) as hereinbefore defined with a compound of the formula (XI) as hereinbefore defined; and
1) isolating compound (I).

In a further aspect, the process described above can further include the step of:

3b) reacting 3-chloro-2-fluoroaniline with ethyl orthoformate to give a compound of formula (XI).

Alternatively, in another aspect of the invention there is provided a process for the preparation of compound (I), or a pharmaceutically acceptable salt thereof, comprising the steps:

2c) reacting a compound of the formula (III) as hereinbefore defined with a compound of the formula (XII) as hereinbefore defined; and
1) isolating compound (I).

The process described above can further include the step of:

3c) reacting 3-chloro-2-fluoroaniline with N,N-dimethylformamide dimethyl acetal to give a compound of formula (XII).

In a further aspect, any of the processes described above can further include the step of:

4) reducing a compound of the formula (IV) as hereinbefore defined to give a compound of the formula (III) as hereinbefore defined.

In a further aspect, any of the processes described above can further include the step of:

5) nitrating a compound of the formula (V) as hereinbefore defined to give a compound of the formula (IV) as hereinbefore defined.

In a further aspect, any of the processes described above can further include the step of:

6) reacting a compound of the formula (VI) as hereinbefore defined with a compound of the formula (VII) as hereinbefore defined to give a compound of the formula (V) as hereinbefore defined.

In a further aspect, the processes described above can further include the step of:

7) deprotecting the compound of the formula (VIII) to give a compound of the formula (VI) as hereinbefore defined.

In a further aspect, any of the processes described above can further include the step of:

8) reacting a compound of the formula (X) as hereinbefore defined with a compound of the formula (IX) as hereinbefore defined to give a compound of the formula (VIII) as hereinbefore defined.

According to another aspect of the invention there is provided a process for the preparation of compound (I), or a pharmaceutically acceptable salt thereof, comprising the steps:
3a) reacting a compound of the formula (III) as hereinbefore defined with N,N-dimethylformamide dimethyl acetal to give a compound of the formula (II) as hereinbefore defined;
2a) reacting the compound of the formula (II) with 3-chloro-2-fluoroaniline in the presence of a suitable acid; and
1) isolating compound (I).

Suitable conditions for steps 1 to 3 are as hereinbefore defined.

According to another aspect of the invention there is provided a process for the preparation of compound (I), or a pharmaceutically acceptable salt thereof, comprising the steps:
4) the reduction of a compound of the formula (IV) as hereinbefore defined to give a compound of the formula (III) as hereinbefore defined;
3a) reacting the compound of the formula (III) with N,N-dimethylformamide dimethyl acetal to give a compound of the formula (II) as hereinbefore defined;
2a) reacting the compound of the formula (II) with 3-chloro-2-fluoroaniline in the presence of a suitable acid; and
1) isolating compound (I).

Suitable conditions for steps 1 to 4 are as hereinbefore defined.

According to another aspect of the invention there is provided a process for the preparation of compound (I), or a pharmaceutically acceptable salt thereof, comprising the steps:
5) the nitration of a compound of the formula (V) as hereinbefore defined to give a compound of the formula (IV) as hereinbefore defined;
4) the reduction of the compound of the formula (IV) to give a compound of the formula (III) as hereinbefore defined;
3a) reacting a compound of the formula (III) with N,N-dimethylformamide dimethyl acetal to give a compound of the formula (II) as hereinbefore defined;
2a) reacting the compound of the formula (II) with 3-chloro-2-fluoroaniline in the presence of a suitable acid; and
1) isolating compound (I).

Suitable conditions for steps 1 to 5 are as hereinbefore defined.

According to another aspect of the invention there is provided a process for the preparation of compound (I), or a pharmaceutically acceptable salt thereof, comprising the steps:
6) the reaction of a compound of the formula (VI) as hereinbefore defined with a compound of the formula (VII) as hereinbefore defined to give a compound of the formula (V) as hereinbefore defined;
5) the nitration of the compound of the formula (V) to give a compound of the formula (IV) as hereinbefore defined;
4) the reduction of the compound of the formula (IV) to give a compound of the formula (III) as hereinbefore defined;
3a) reacting a compound of the formula (III) with N,N-dimethylformamide dimethyl acetal to give a compound of the formula (II) as hereinbefore defined;
2a) reacting the compound of the formula (II) with 3-chloro-2-fluoroaniline in the presence of a suitable acid; and
1) isolating compound (I).

Suitable conditions for steps 1 to 6 are as hereinbefore defined.

According to another aspect of the invention there is provided a process for the is preparation of compound (I), or a pharmaceutically acceptable salt thereof, comprising the steps:
8) the reaction of a compound of the formula (X) as hereinbefore defined with a compound of the formula (IX) as hereinbefore defined to give a compound of the formula (VIII) as hereinbefore defined;
7) deprotecting the compound of the formula (VIII) to give a compound of the formula (VI) as hereinbefore defined;
6) the reaction of the compound of the formula (VI) with a compound of the formula (VII) as hereinbefore defined to give a compound of the formula (V) as hereinbefore defined;
5) the nitration of the compound of the formula (V) to give a compound of the formula (IV) as hereinbefore defined;
4) the reduction of the compound of the formula (IV) to give a compound of the formula (III) as hereinbefore defined;
3a) reacting a compound of the formula (III) with N,N-dimethylformamide dimethyl acetal to give a compound of the formula (II) as hereinbefore defined;
2a) reacting the compound of the formula (II) with 3-chloro-2-fluoroaniline in the presence of a suitable acid; and
1) isolating compound (I).

Suitable conditions for steps 1 to 8 are as hereinbefore defined.

In any of the above processes, steps 2a) and 3a) can be replaced with the following steps 2b) and 3b):
2b) reacting a compound of the formula (III) as hereinbefore defined with a compound of the formula (XI) or (XII) as hereinbefore defined; and/or
3b) reacting 3-chloro-2-fluoroaniline with ethyl orthoformate to give a compound of formula (XI).

In any of the above processes, steps 2a) and 3a) can also be replaced with the following steps 2c) and 3c):
2c) reacting a compound of the formula (III) as hereinbefore defined with a compound of the formula (XII) as hereinbefore defined; and/or
3c) reacting 3-chloro-2-fluoro aniline with N,N-dimethylformamide dimethyl acetal to give a compound of formula (XII).

If desired compound (I) may be converted into a pharmaceutically acceptable salt. WO2005/028469 describes examples of salts of compound (I), such as an acid-addition salt of compound (I) with an inorganic or organic acid such as hydrochloric, hydrobromic, sulfuric, trifluoroacetic, citric or maleic acid. A particular salt is a difumarate salt of compound (I) as described in the examples.

Certain intermediates used in the processes according to the invention are novel and form a further aspect of the present invention. Intermediates provided herein, or salts thereof, can have the following structure:

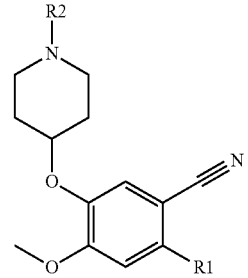

XIII wherein:
R1 is H, —NH$_2$, —NO$_2$, or

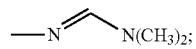

R2 is H, N-methylcarbamoylmethyl, or Pg$^1$, and
Pg$^1$ is an amino protecting group;

with the proviso that when R2 is H or an amino protecting group then R1 is H.

Accordingly another aspect of the invention provides a compound selected from any one of compounds of the formula (II), (III), (IV), (V), (VI), and (VIII), or a salt thereof. Another aspect of the invention provides a compound of the formula (XI), or a salt thereof. Another aspect of the invention provides a compound of the formula (XII), or a salt thereof.

In one embodiment there is provided a compound wherein $Pg^1$ is tert-butoxycarbonyl, for example in a compound of the formula (VIII).

The compound described herein, including those of formulas (II), (XI) and (XII), may have a geometric isomeric centre and may exist as the E- and Z-isomers. It is to be understood that the present invention encompasses all such geometric isomers and mixtures thereof. In one embodiment of the invention the compound of the formula (II) is substantially present as the E-isomer. In another embodiment of the invention the compound of the formula (II) is substantially present as the Z-isomer. In one embodiment of the invention the compound of the formula (XI) is substantially present as the E-isomer. In another embodiment of the invention the compound of the formula (XI) is substantially present as the Z-isomer. In one embodiment of the invention the compound of the formula (XII) is substantially present as the E-isomer. In another embodiment of the invention the compound of the formula (XII) is substantially present as the Z-isomer.

The intermediates may be used as the free base or in the form of a suitable salt. Such salts include both pharmaceutically acceptable salts and salts that are not pharmaceutically acceptable. The use of intermediates in the form of a salt that is not pharmaceutically acceptable may be advantageous in the processes according to the invention. For example such salts may be useful for isolation or purification of the intermediates. If required the intermediates can be modified by conventional techniques to give a pharmaceutically acceptable salt of the compound. Such techniques are well known to those skilled in the art and include, for example ion exchange techniques or re-precipitation of the compound in the presence of a pharmaceutically acceptable counter ion. It is to be understood therefore that the present invention is intended to cover the intermediates and salts thereof.

The compound (I) and salts thereof such as the difumarate salt is suitably administered to patients orally in the form of a suitable pharmaceutical composition, for example a tablet, capsule or granule formulation.

For example compound (I) difumarate is suitably formulated as a tablet using the following excipients:
Tablet Core:
  Compound (I) difumarate (for example Form A);
  lactose;
  microcrystalline cellulose;
  crospovidone;
  polyvidone (PVP); and
  magnesium stearate The tablet core may be coated with a film-coating, such as an HPMC based film coating, which coating optionally contains one or more colorants and/or light protective agents.

The tablets may be prepared using conventional methods and as illustrated in the Examples.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 200 mg, for example from 1 to 100 mg) compounded with an appropriate and convenient amount of excipients which may vary from about 5 to about 98 percent by weight of the total composition.

The size of the dose for therapeutic or prophylactic purposes of compound (I) and salts thereof such as the difumarate salt will naturally vary according to the nature and severity of the conditions, the age and sex of the animal or patient and the route of administration, according to well known principles of medicine. In one embodiment a suitable dose of compound (I) for use in the treatment of a cancer such as breast cancer is 40, 80, 100, 160, 200 or 240 mg twice daily.

Compound (I) possesses anti-proliferative properties such as anti-cancer properties that are believed to arise from their erbB family receptor tyrosine kinase inhibitory activity, and particularly a mixed erbB2/EGF and/or erbB3/EGF profile.

Accordingly, the compounds of the present invention are expected to be useful in the treatment of diseases or medical conditions mediated alone or in part by erbB receptor tyrosine kinases. Accordingly the compounds of the present invention are expected to be useful in the treatment of psoriasis, benign prostatic hyperplasia (BPH), atherosclerosis and restenosis and/or cancer by providing an anti-proliferative effect, particularly in the treatment of erbB receptor tyrosine kinase sensitive cancers. Such benign or malignant tumours may affect any tissue and include non-solid tumours such as leukaemia, multiple myeloma or lymphoma, and also solid tumours, for example bile duct, bone, bladder, brain/CNS, breast, colorectal, endometrial, gastric, head and neck, hepatic, lung, neuronal, oesophageal, ovarian, pancreatic, prostate, renal, skin, testicular, thyroid, uterine and vulval cancers. In particular compound (I) is expected to be useful in the treatment of breast cancer.

Compound (I) and salts thereof such as the difumarate may be used in the treatment of estrogen and/or progesterone positive breast cancer in combination with an effective amount of an aromatase inhibitor such as anastrozole. This combination may be particularly beneficial in the treatment of patients that have not previously been treated with an endocrine therapy such as for example, a selective estrogen receptor modulator such as tamoxifen, an aromatase inhibitor such as anastrozole or an estrogen receptor down-regulator.

Compound (I) and salts thereof such as a difumarate salt may also be used in combination with a taxane such as paclitaxel or docetaxel. This combination may be useful in the treatment of breast cancer. For example, in the treatment of a breast cancer which has a low over-expression of erbB2. The term "low over-expression of erbB2" refers to tumours that are Her2 fluorescent in-situ hybridization (FISH) negative. Particular tumours that are "low over-expression of erbB2" those that are:
  (i) Her2+ by immunohistochemistry (IHC); and/or
  (ii) Her2++ by IHC and Her2 fluorescent in-situ hybridization (FISH) negative.

LEGENDS TO FIGURES

EXAMPLES

Figure 1:
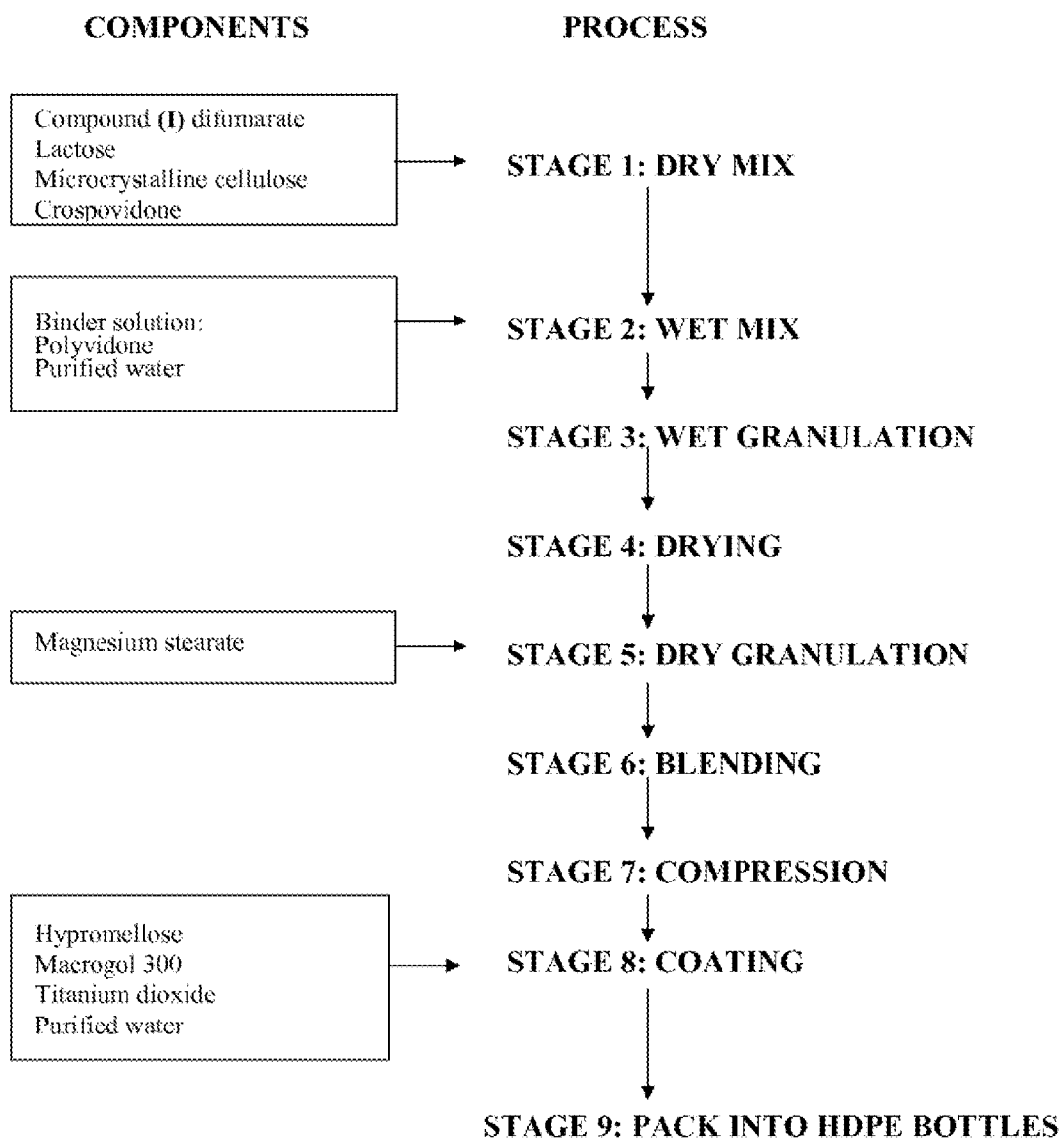
FIG. 1 shows an X-ray powder diffraction pattern (XRPD) for compound (I) difumarate Form A. The x-axis shows the 2-theta value and the y-axis the counts.

The invention is further illustrated by way of the following examples, which are intended to elaborate several embodiments of the invention. These examples are not intended to, nor are they to be construed to, limit the scope of the invention. It will be clear that the invention may be practiced otherwise than as particularly described herein. Numerous modifications and variations of the present invention are possible in view of the teachings herein and, therefore, are within the scope of the invention.

In the Examples unless otherwise stated:—

(i) yields are given for illustration only and are not necessarily the maximum attainable;

(ii) melting points were determined by DSC analysis using a Mettler DSC820e apparatus; 1-2 mg samples were accurately weighed and analysed in a vented sample pan; heating was carried out at 10° C./min from 25° C. to 325° C.; unless states otherwise melting points herein refer to the onset temperature of the melting endotherm measured using DSC;

(iii) mass spectra were run with an electron energy of 70 electron volts in the chemical ionization (CI) mode using a direct exposure probe; where indicated ionization was effected by electron impact (EI), fast atom bombardment (FAB) or electrospray (ESP); values for m/z are given; generally, only ions which indicate the parent mass are reported; and unless otherwise stated, the mass ion quoted is $(M+H)^+$ which refers to the protonated mass ion; reference to $M^+$ is to the mass ion generated by loss of an electron; and reference to $(M-H)^-$ is to the mass ion generated by loss of a proton;

(iv) when given, NMR data is in the form of delta values for major diagnostic protons, given in parts per million (ppm) relative to tetramethylsilane (TMS) as an internal standard, determined at 500 MHz using perdeuterio dimethyl sulfoxide (DMSO-$d_6$) as solvent unless otherwise indicated; the following abbreviations have been used: s, singlet; d, doublet; t, triplet; q, quartet; m, multiplet; br, broad;

(v) chemical symbols have their usual meanings; SI units and symbols are used;

(vi) solvent ratios are given in volume:volume (v/v) terms;

Example 1

Preparation of 4-(3-Chloro-2-fluoroanilino)-7-methoxy-6-{[1-(N-methylcarbamoylmethyl)piperidin-4-yl]oxy}quinazoline (Compound (I))

Compound (I) was prepared according to the scheme shown below:

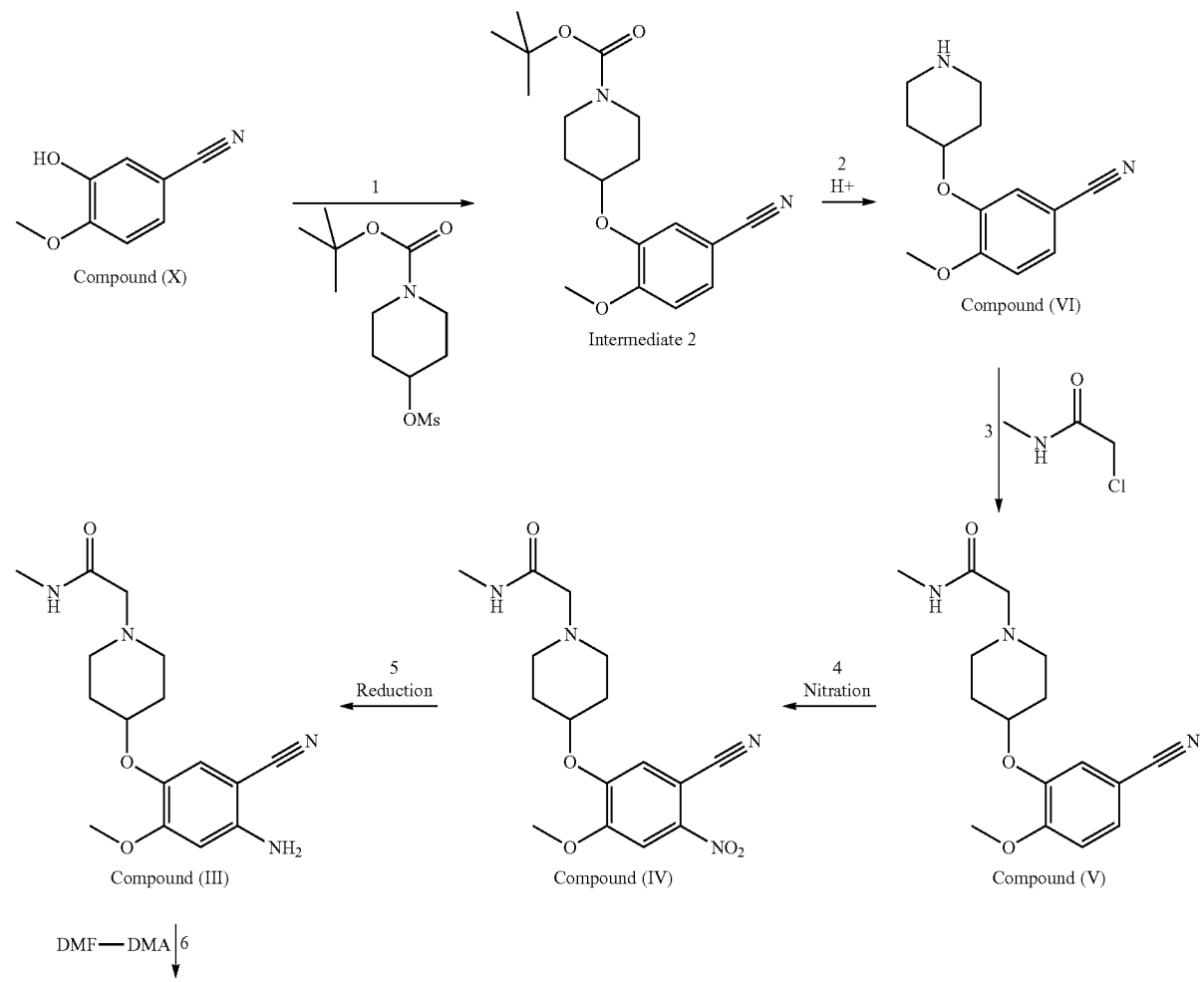

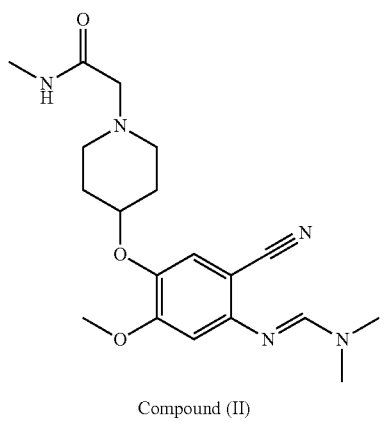

Compound (II)

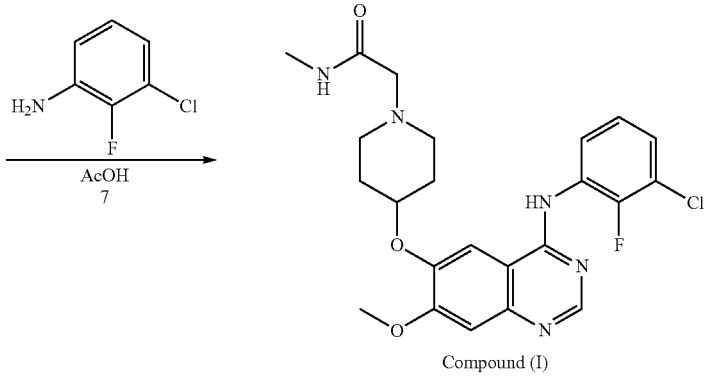

Compound (I)

Step 1. Preparation of tert-butyl 4-(5-cyano-2-methoxyphenoxy)piperidine-1-carboxylate (Intermediate 2). 3-hydroxy-4-methoxybenzonitrile (Compound (X), 6.00 g, 39.62 mmole), tert-butyl (4-methanesulfonyloxy)piperidine-1-carboxylate (16.6 g, 59.44 mmoles) (Chemical & Pharmaceutical Bulletin 2001, 49(7), 822-829); and potassium carbonate (6.71 g, 47.55 mmoles) were suspended in isopropanol (78.98 g) and the mixture was heated at reflux with stirring. Additional tert-butyl (4-methanesulfonyloxy)piperidine-1-carboxylate (2.08 g, 7.43 mmoles) was added to push the reaction to completion. The mixture was then cooled and quenched by the addition of water (100.47 g). Seeding with intermediate 2 followed by cooling to 0° C. resulted in a crystalline product, which was isolated by filtration. The filter cake was washed with a mixture of water (8.86 g) and isopropanol (6.97 g), followed by water (23.64 g) and then dried to give Intermediate 2 (10.75 g, 80% yield); $^1$H NMR (400 MHz, DMSO-$d_6$) δ ppm 1.39 (s, 9H) 1.48 (m, 2H) 1.88 (m, 2H) 3.13 (m, 2H) 3.67 (m, 2H) 3.83 (s, 3H) 4.56 (tt, J=8.1, 3.8 Hz, 1H) 7.13 (d, J=8.4 Hz, 1H) 7.42 (dd, J=8.4, 1.9 Hz, 1H) 7.51 (d, J=1.9 Hz, 1H); Mass Spectrum: m/z (M+H)$^+$ 333.1.

Step 2. Preparation of 4-methoxy-3-(piperidin-4-yloxy) benzonitrile (Compound (VI)). Intermediate 2 (39.31 g, 118.26 mmoles) was suspended in ethanol (155.53 g) and heated to 40° C. To this slurry was slowly added HCl (46.61 g, 573.04 mmoles). The mixture was heated to 60° C. and held for 3 hours. The reaction mixture was cooled to 20° C. and seed was charged initiating crystallisation. The resulting solid was isolated by filtration at 0° C., washed twice with ethanol (62.21 g) and then dried to give compound (VI) as the hydrochloride salt (29.84 g, 77% yield); $^1$H NMR (400 MHz, DMSO-$d_6$) δ ppm 1.84 (m, 2H) 2.09 (m, 2H) 3.02 (ddd, J=12.7, 8.9, 3.4 Hz, 2H) 3.20 (m, 2H) 3.84 (s, 3H) 4.63 (tt, J=7.7, 3.6 Hz, 1H) 7.15 (d, J=8.5 Hz, 1H) 7.45 (dd, J=8.5, 1.9 Hz, 1H) 7.56 (d, J=1.9 Hz, 1H) 9.16 (br. s, 2H); Mass Spectrum: m/z (M+H)$^+$ 233.2.

Step 3. Preparation of 2-[4-(5-cyano-2-methoxyphenoxy) piperidin-1-yl]-N-methylacetamide (Compound (V)). Compound (VI) (28.36 g, 95.82 mmoles), 2-chloro-N-methylacetamide (12.37 g, 114.98 mmoles) and potassium carbonate (33.11 g, 239.55 mmoles) were suspended in acetonitrile (161.36 g). The reaction mixture was heated at reflux for 3 hours. The reaction mixture was cooled to 20° C. and water (386.26 g) was charged. The reaction was heated to 75° C. and the volume reduced by distillation. Upon cooling crystallisation occurred. The resulting solid was isolated by filtration, washed twice with water (77.25 g and 128.75 g) and then dried to give compound (V) (27.95 g, 94% yield); $^1$H NMR (400 MHz, DMSO-$d_6$) δ ppm 1.68 (m, 2H) 1.91 (m, 2H) 2.29 (m, 2H) 2.61 (d, J=4.7 Hz, 3H) 2.67 (m, 2H) 2.88 (s, 2 H) 3.83 (s, 3H) 4.41 (tt, J=8.3, 4.0 Hz, 1H) 7.11 (d, J=8.4 Hz, 1H) 7.40 (dd, J=8.4, 1.9 Hz, 1H) 7.47 (d, J=1.9 Hz, 1H) 7.68 (q, J=4.7 Hz, 1H); Mass Spectrum: m/z (M+H)$^+$ 304.2.

Step 4. Preparation of 2-[4-(5-cyano-2-methoxy-4-nitrophenoxy)piperidin-1-yl]-N-methylacetamide (Compound (IV)). Compound (V) (8.78 g, 26.11 mmoles) was suspended in acetic acid (22.82 g, 364.87 mmoles) and the resulting reaction mixture cooled to 5° C. To this was added sulfuric acid (23.64 g, 234.95 mmoles) maintaining the reaction temperature below 30° C. To the resulting solution was added nitric acid (2.40 g, 26.63 mmoles). The reaction mixture was then heated to 35° C. and held for 3 hours. Additional nitric acid (117 mg, 1.31 mmoles) and sulphuric acid (1.31 g 13.1 mmoles) were charged and the reaction mixture was heated at 35° C. for 30 minutes. The solution was cooled to 20° C. and quenched with aqueous ammonia (92.45 g 1.36 moles), resulting in an increase in temperature to 50° C. To the resulting slurry was added, propionitrile (61.58 g 1.12 moles) and water (19 g). The reaction mixture was heated to 80° C. resulting in a clear solution, which upon settling gave two layers. The bottom layer was removed. The reaction mixture was cooled to 20° C. resulting in a thick slurry. The solid was isolated by filtration, washed with propionitrile (6.16 g 112.0 mmoles) and dried to afford compound (IV) (7.44 g, 82% yield); $^1$H NMR (400 MHz, DMSO-$d_6$) δ ppm 1.72 (m, 2H) 1.97 (m, 2H) 2.35 (m, 2H) 2.61 (d, J=4.7 Hz, 3H) 2.66 (m, 2H) 2.90 (s, 2H) 3.96 (s, 3H) 4.73 (tt, J=8.4, 4.0 Hz, 1H) 7.71 (q, J=4.7 Hz, 1H) 7.82 (s, 1H) 7.86 (s, 1H). Mass Spectrum: m/z (M+H)$^+$ 349.2

Step 5. Preparation of 2-[4-(4-amino-5-cyano-2-methoxyphenoxy)piperidin-1-yl]-N-methylacetamide (Compound (III)). Compound (N) (7.42 g, 19.38 mmoles) was suspended in water (44.52 g) and methanol (5.35 g). To this was added sodium dithionite (11.91 g, 58.15 mmoles) and the resulting reaction mixture was heated to 60° C. To the reaction mixture was added hydrochloric acid (46.98 g, 463.89 mmoles)), resulting in a solution, which was held at 60° C. for 3 hours. The reaction mixture was then allowed to cool to 20° C. Aqueous sodium hydroxide (15.51 g 182.2 mmoles) was charged followed by 2-methyltetrahydrofuran (58.0 g). The reaction mixture was heated to 60° C., which upon settling gave two layers and the lower aqueous layer was discarded. The volume of the reaction mixture was reduced by vacuum distillation and methyl tert-butyl ether (18.54 g) was added to give a slurry which was cooled to 10° C. and then the solid was collected by filtration. The solid was washed with 2-methyltetrahydrofuran (5.8 g) and dried to give compound (III) (5.4 g, 78% yield); $^1$H NMR (400 MHz, DMSO-$d_6$) δ ppm 1.62 (m, 2H) 1.82 (m, 2H) 2.20 (m, 2H) 2.60 (d, J=4.7 Hz, 3H) 2.65 (m, 2H) 2.86 (s, 2H) 3.72 (s, 3H) 4.00 (tt, J=8.3, 4.0 Hz, 1H) 5.66 (br. s, 2H) 6.39 (s, 1H) 6.94 (s, 1H) 7.65 (q, J=4.7 Hz, 1H). Mass Spectrum: m/z (M+H)+ 319.2.

Step 6. Preparation of 2-[4-(5-cyano-4-{[(dimethylamino) methylene]amino}-2-methoxyphenoxy)piperidin-1-yl]-N-methylacetamide (Compound (II)). Compound (III) (18.21 g, 52.05 mmoles) was suspended in 2-methyltetrahydrofuran (99.62 g). To this was added acetic acid (162.79 mg), and N,N-dimethylformamide dimethyl acetal (DMA) (8.63 g, 70.27 mmoles) and the resulting reaction mixture was heated at 76° C. for 16 hrs. Additional N,N-dimethylformamide dimethyl acetal (639.41 mg, 5.20 mmoles) was added to the reaction mixture to ensure the reaction completed. The reaction mixture was cooled to 30° C. during which time crystallisation occurred. The resulting solid was isolated by filtration, washed with 2-methyltetrahydrofuran (14.23 g) and dried to afford compound (II) (19.53 g, 97% yield); $^1$H NMR (400 MHz, DMSO-d$_6$) δ ppm 1.65 (m, 2H) 1.86 (m, 2H) 2.24 (m, 2H) 2.60 (d, J=4.7 Hz, 3H) 2.66 (m, 2H) 2.87 (s, 2H) 2.95 (s, 3H) 3.04 (s, 3H) 3.81 (s, 3H) 4.19 (tt, J=8.2, 3.8 Hz, 1H) 6.72 (s, 1H) 7.15 (s, 1H) 7.67 (q, J=4.7 Hz, 1H) 7.90 (s, 1H); Mass Spectrum: m/z (M+H)+ 374.2.

Step 7. Preparation of compound (I). 2-[4-(5-cyano-4-{[(dimethylamino)methylene]amino}-2-methoxyphenoxy) piperidin-1-yl]-N-methylacetamide (compound (II), 7.00 g, 17.71 mmoles), was suspended in methoxybenzene (35.8 g). Acetic acid (16.6 g) was charged and to the resulting solution was added 3-chloro-2-fluoroaniline (2.71 g, 18.07 mmoles). The reaction mixture was heated at 90° C. for 20 hours then cooled to 20° C. Water (37.04 g) was charged to the reaction mixture, and the organic layer discarded. To the resulting aqueous mixture was charged isopropanol (39.00 g), followed by aqueous ammonia (20.79 g, 25%). The reaction mixture was heated to 30° C. and seeded with compound (I), which induced crystallisation. The reaction was then cooled to 0° C. and the product isolated by filtration. The filter cake was washed twice with a mixture of water (7.28 g) and isopropanol (4.68 g), then dried to afford the compound (I) (5.65 g, 55% yield); $^1$H NMR (400 MHz, DMSO-d$_6$) δ ppm 1.79 (m, 2H) 2.04 (m, 2H) 2.38 (m, 2H) 2.62 (d, J=4.5 Hz, 3H) 2.74 (m, 2H) 2.94 (s, 2H) 3.93 (s, 3H) 4.56 (tt, J=8.1, 3.8 Hz, 1H) 7.21 (s, 1H) 7.28 (m, 1H) 7.50 (m, 2H) 7.73 (q, J=4.5 Hz, 1H) 7.81 (s, 1H) 8.36 (s, 1H) 9.56 (br.s, 1H); Mass Spectrum: m/z (M+H)+ 474.2, 476.2.

Example 2

Preparation of 4-(3-Chloro-2-fluoroanilino)-7-methoxy-6-{[1-(N-methylcarbamoylmethyl)piperidin-4-yl]oxy}quinazoline (Compound (I))

Compound (I) was prepared according to the scheme shown below:

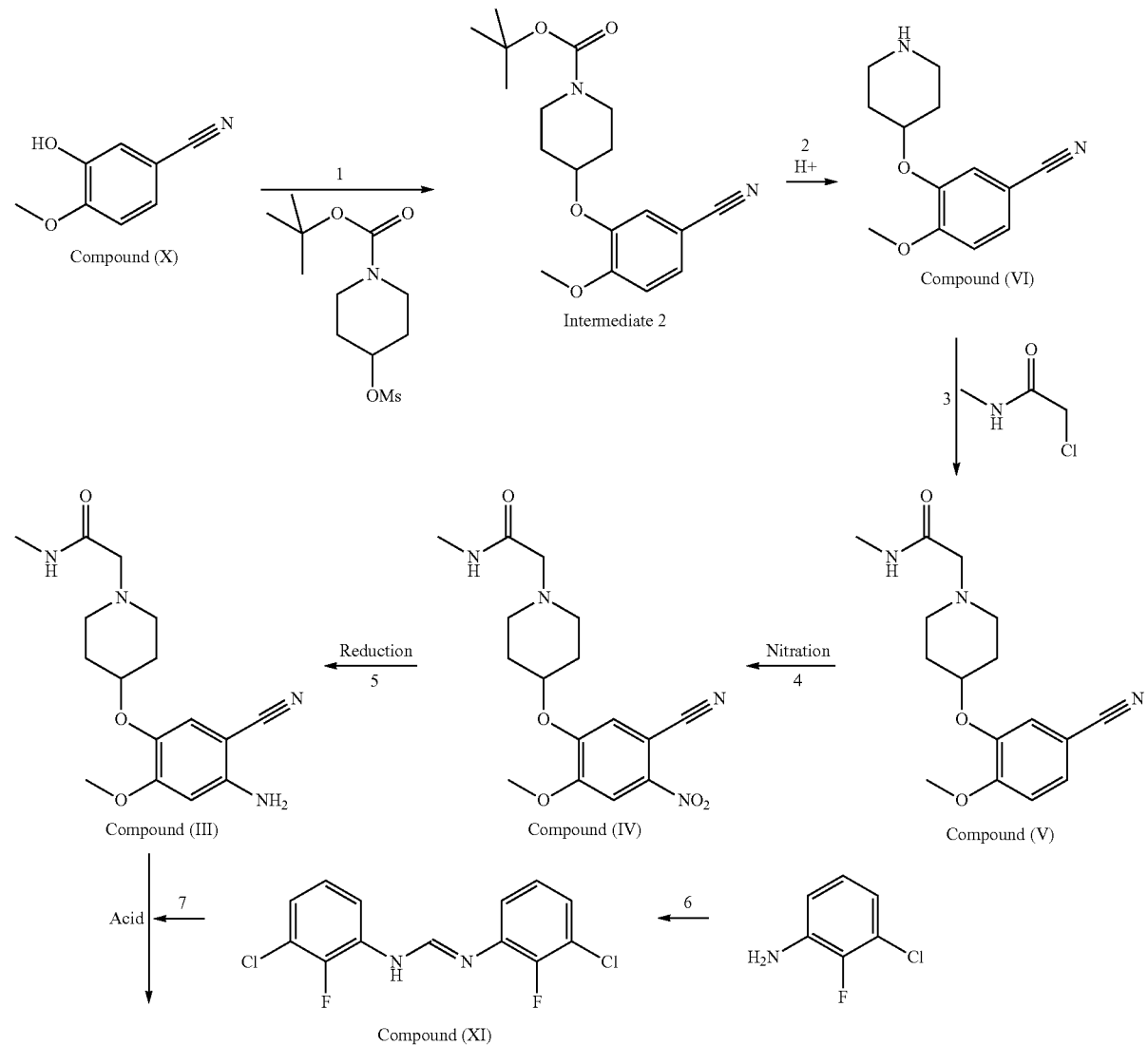

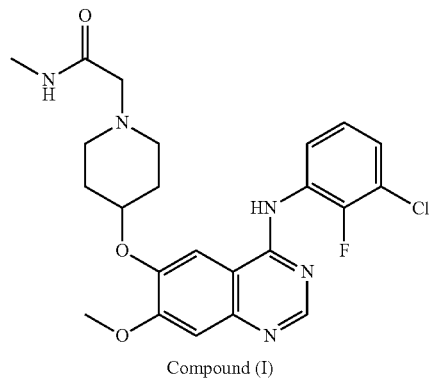

Compound (I)

Steps 1, 2, 3 and 4 as set forth in Example 1.

Step 5, alternate 1. Preparation of compound (III). 2-[4-(5-Cyano-2-methoxy-4-nitrophenoxy)piperidin-1-yl]-N-methylacetamide (compound (IV), 15.00 g, 42.50 mmoles) was suspended in water (90.00 g) and methanol (59.38 g). To this was added sodium dithionite (30.47 g, 148.75 mmoles) and water (90.00 g), the resulting reaction mixture was heated to 30° C. and held for 2 hrs. To the reaction mixture was added hydrochloric acid (27.98 g, 276.25 mmoles)), resulting in a solution, which was held at 60° C. for 2 hours. Aqueous sodium hydroxide (30.60 g 382.49 mmoles) was added followed by a line wash of water (30.00 g). The reaction mixture was cooled to 25° C. to give a slurry which was collected by filtration. The solid was washed with water (30.00 g) and dried to give compound (III) (13.50 g, 82% yield); $^1$H NMR (400 MHz, DMSO-d$_6$) δ ppm 1.62 (m, 2H) 1.82 (m, 2H) 2.20 (m, 2H) 2.60 (d, J=4.7 Hz, 3H) 2.65 (m, 2H) 2.86 (s, 2H) 3.72 (s, 3H) 4.00 (tt, J=8.3, 4.0 Hz, 1H) 5.66 (br. s, 2H) 6.39 (s, 1H) 6.94 (s, 1H) 7.65 (q, J=4.7 Hz, 1H). Mass Spectrum: m/z (M+H)$^+$ 319.2.

Step 5, alternate 2. Preparation of compound (III). Compound (IV) (8.00 g, 22.67 mmoles) and 1% platinum+2% vanadium catalyst on carbon (1.23 g, 0.023 mmoles) were to suspended in Acetonitrile (94.00 g). The reaction mixture was hydrogenated at a pressure of 3 Bar G and at a temperature of 35° C. for 3 hrs. Once complete, the reaction mixture was filtered to remove the catalyst which is washed with acetonitrile (31.33 g). The volume of the reaction mixture was reduced by vacuum distillation to give a slurry which was cooled to 0° C. and then the solid was collected by filtration. The solid was washed with acetonitrile (12.53 g) and dried to give compound (III) (5.88 g, 78% yield); $^1$H NMR (400 MHz, DMSO-d$_6$) δ ppm 1.62 (m, 2H) 1.82 (m, 2H) 2.20 (m, 2H) 2.60 (d, J=4.7 Hz, 3H) 2.65 (m, 2H) 2.86 (s, 2H) 3.72 (s, 3H) 4.00 (tt, J=8.3, 4.0 Hz, 1H) 5.66 (br. s, 2H) 6.39 (s, 1H) 6.94 (s, 1H) 7.65 (q, J=4.7 Hz, 1H). Mass Spectrum: m/z (M+H)$^+$ 319.2.

Step 6. Preparation of N,N'-bis(3-chloro-2-fluorophenyl) imidoformamide (compound (XI)). 3-chloro-2-fluoroaniline (51.21 g, 341.22 mmoles) was suspended in cyclohexane (87.07 g). To this ethyl orthoformate (22.28 g, 150.32 mmoles) and acetic acid (0.94 g, 15.03 mmoles) were added. The resulting reaction mixture was heated, with stirring, to 48° C. for 12 hours. Following this the reaction mixture was cooled to 20° C. over 12 hours and the solid product was isolated by filtration. The filter cake was washed with cylcohexane (26.12 g) and dried in vacuo at 40° C. to give compound (XI) as a white crystalline product (33.95 g, 93% yield); 1H NMR Spectrum (400 MHz, DMSO-d6) δ ppm 7.14 (t, 2H) 7.22 (m, 2H) 8.14 (s, 1H), 9.98 (s, 1H); Mass Spectrum (by GC-MS EI): m/z (M$^+$) 300.0.

Figure 2:
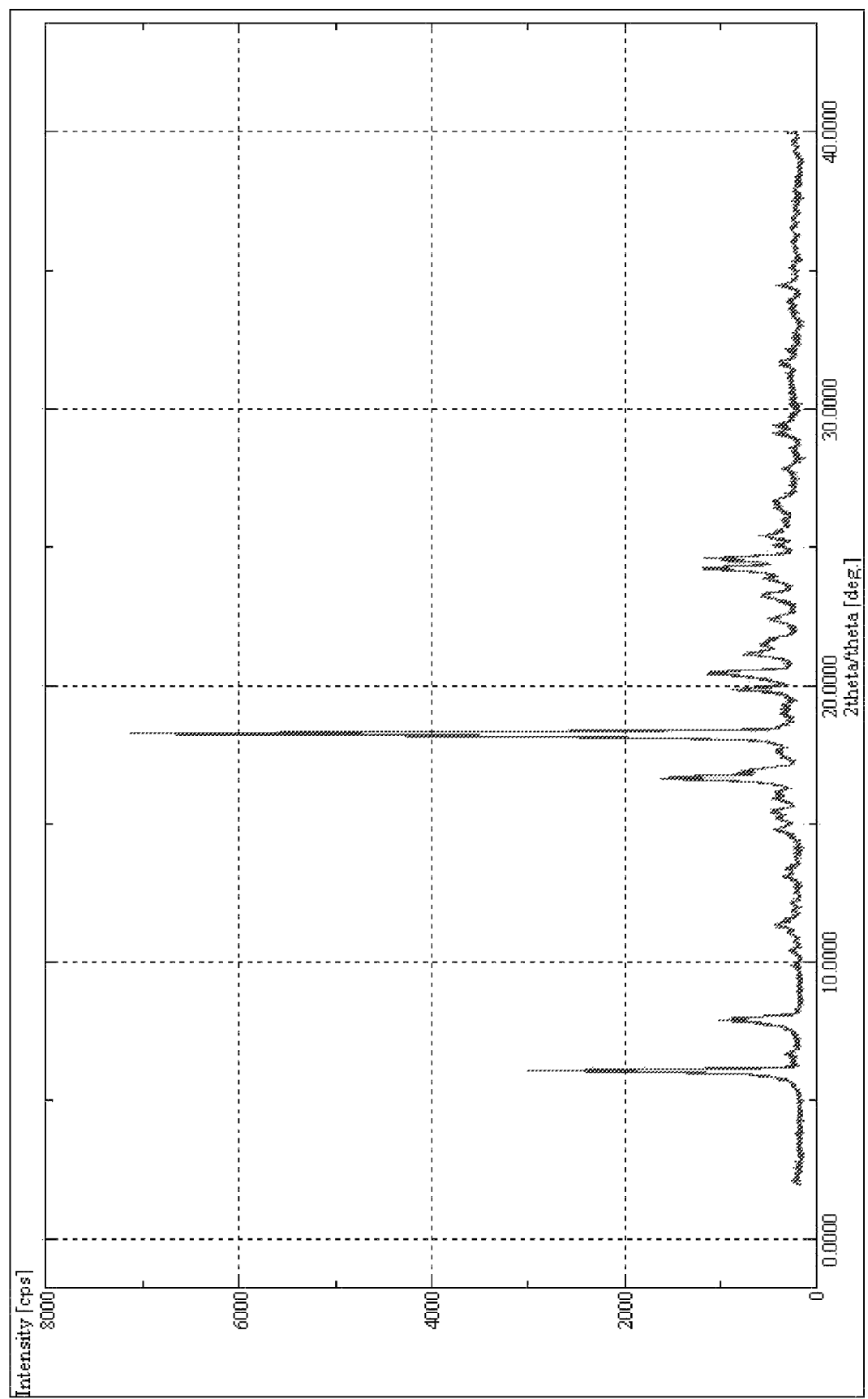
FIG. 2 shows an X-ray powder diffraction pattern (XRPD) for compound (I) as a 2-methyltetrahydrofuran solvate. The x-axis shows the 2-theta value and the y-axis the counts.

Step 7, alternate 1: Preparation of compound (I). 2-[4-(4-Amino-5-cyano-2-methoxyphenoxy)piperidin-1-yl]-N-methylacetamide (compound (III)) (10 g, 29.84 mmol) and N,N'-bis(3-chloro-2-fluorophenyl)imidoformamide (compound (XI)) (11.46 g, 37.3 mmol) were suspended in 2-methyltetrahydrofuran (30.4 ml) and heated to 80° C. To this yellow suspension was added acetic acid (7.6 ml, 127.33 mmol) and the resulting solution was heated to 92° C. for 6 hours. 2-methyltetrahydrofuran (66.5 ml) and water (28.5 ml) were added and mixture was cooled to 55° C. before adding 50% w/w sodium hydroxide (7 ml, 131.29 mmol) resulting in a temperature rise to 63° C. The temperature was raised further to 69° C. and after settling the aqueous phase was discarded. The organic phase was washed with water (3×20 ml) and each aqueous phase was discarded after settling. 2-methyltetrahydrofuran (100 ml, 997 mmol) was added and the volume reduced by distillation. Seed was added to induce crystallisation and the resulting mixture was cooled to 15° C. The crystalline form was initially obtained following a spontaneous crystallisation from the experiment as described. The resulting solid was isolated by filtration, washed twice with 2-methyltetrahydrofuran (19 ml) and dried under vacuum at 40° C. to yield compound (I) as a white solid (12.14 g, 95%). $^1$H NMR (400 MHz, DMSO-d$_6$) δ ppm 1.12 (d, J=6 Hz, 1.3H), 1.26-1.36 (m, 0.4H), 1.75-1.97 (m, 3.3H), 2.02-2.15 (m, 2H), 2.35-2.44 (m, 2H), 2.64 (d, J=4.7 Hz, 3H), 2.72-2.80 (m, 2H), 2.95 (s, 2H), 3.52-3.59 (m, 0.4H), 3.72-3.87 (m, 0.86H), 3.95 (s, 3H), 4.53-4.63 (m, 1H), 7.22 (s, 1H), 7.29 (dt J=1 Hz J=8 Hz, 1H), 7.51 (dt J=7.4 Hz, J=18 Hz, 2H), 7.71-7.77 (m, 1H), 7.82 (s, 1H), 8.37 (s, 1H), 9.57 (s, 1H). Mass Spectrum: m/z (M+H)+ 474.0. The NMR data above includes signals for the 2-methyltetrahydrofuran solvent which is present in a 0.43 molar equivalence. The signals pertaining to the solvent are at δ ppm shifts of 1.12, 1.26-1.36, 3.52-3.59 and 3.72-3.87. The cluster at 1.75-1.93 contains signals for the solvent and the parent compound. The XRPD for this compound is shown in FIG. 2.

Figure 3:
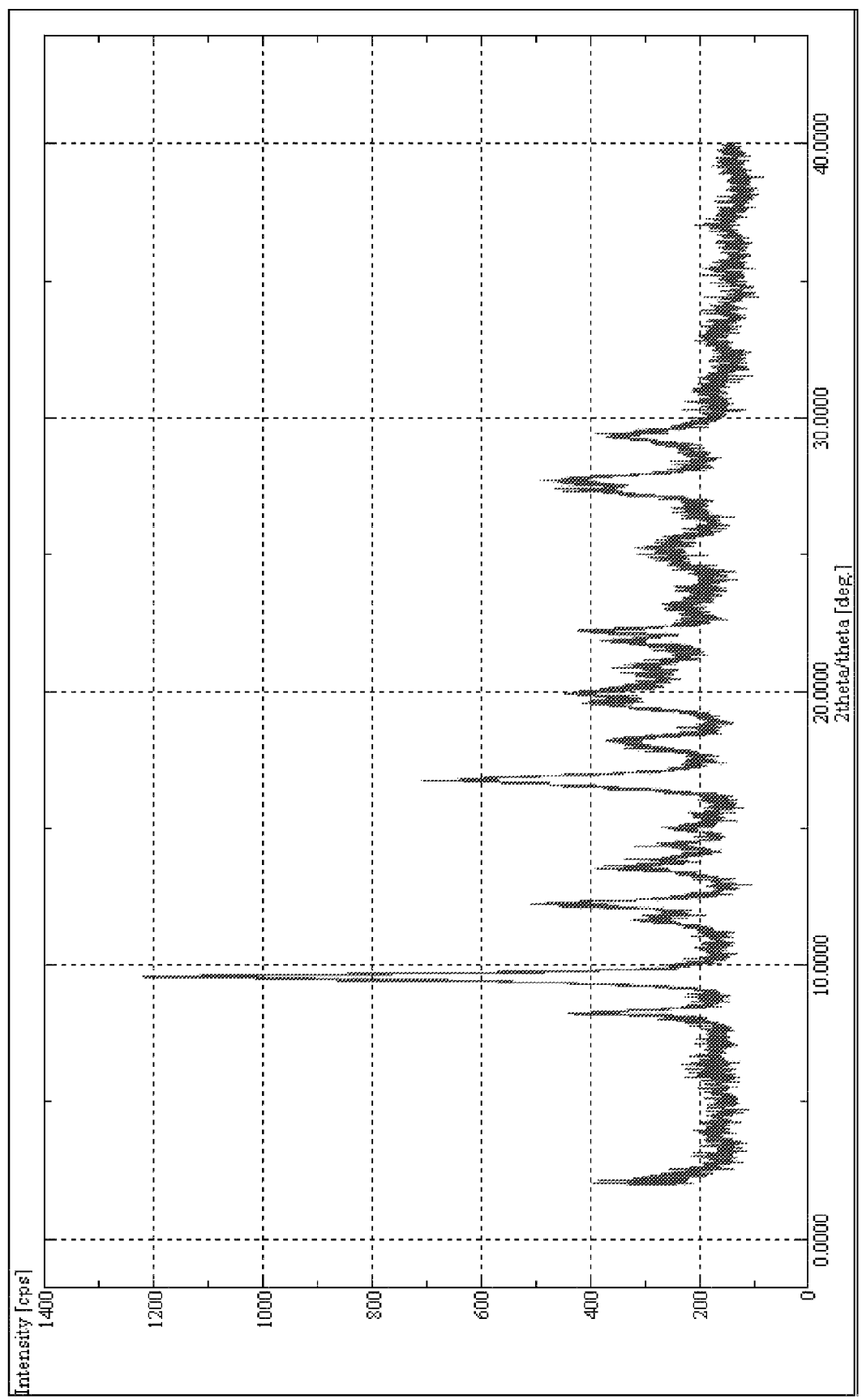
FIG. 3 shows an X-ray powder diffraction pattern (XRPD) for compound (I) as a hydrate. The x-axis shows the 2-theta value and the y-axis the counts.

Step 7, alternate 2. Preparation of compound (I). Compound (III) (15 g, 44.76 mmol) and compound (XI) (17.19 g, 55.95 mmol) were suspended in 2-methyltetrahydrofuran (45.6 ml) and heated to 83° C. To this yellow suspension was added acetic acid (11.4 ml, 190.99 mmol) and the resulting solution was heated to 92° C. for 3½ hours. 2-methyltetrahydrofuran (105 ml) and water (50 ml) were added and mixture was cooled to 49° C. before adding 50% w/w sodium hydroxide (10.74 ml, 201.4 mmol), resulting in a temperature rise to 62° C. The temperature was maintained at 62° C. and after settling the aqueous phase was discarded. The organic phase was washed with water (3×30 ml) and each aqueous phase was discarded after settling. The mixture was cooled to 15° C. and seed was added to induce crystallisation. The crystalline form was initially obtained following a spontaneous crystallisation from the experiment as described. The resulting solid was isolated by filtration, washed twice with 2-methyltetrahydrofuran (21 ml) and dried under vacuum at 40° C. to yield compound (I) as a white solid (20.12 g, 95%). $^1$H NMR (400 MHz, DMSO-d$_6$) δ ppm 1.75-1.86 (m, 2H), 2.02-2.15 (m, 2H), 2.35-2.44 (m, 2H), 2.64 (d, 1-=4.7 Hz, 3H), 2.72-2.80 (m, 2H), 2.95 (s, 2H), 3.95 (s, 3H), 4.53-4.63 (m, 1H), 7.22 (s, 1H), 7.29 (dt J=1 Hz J=8 Hz, 1H), 7.51 (dt J=7.4 Hz, J=18 Hz, 2H), 7.71-7.77 (m, 1H), 7.82 (s, 1H), 8.37 (s, 1H), 9.57 (s, 1H). Mass Spectrum: m/z (M+H)+ 474.0. The XRPD for this compound is shown in FIG. 3.

Figure 4:
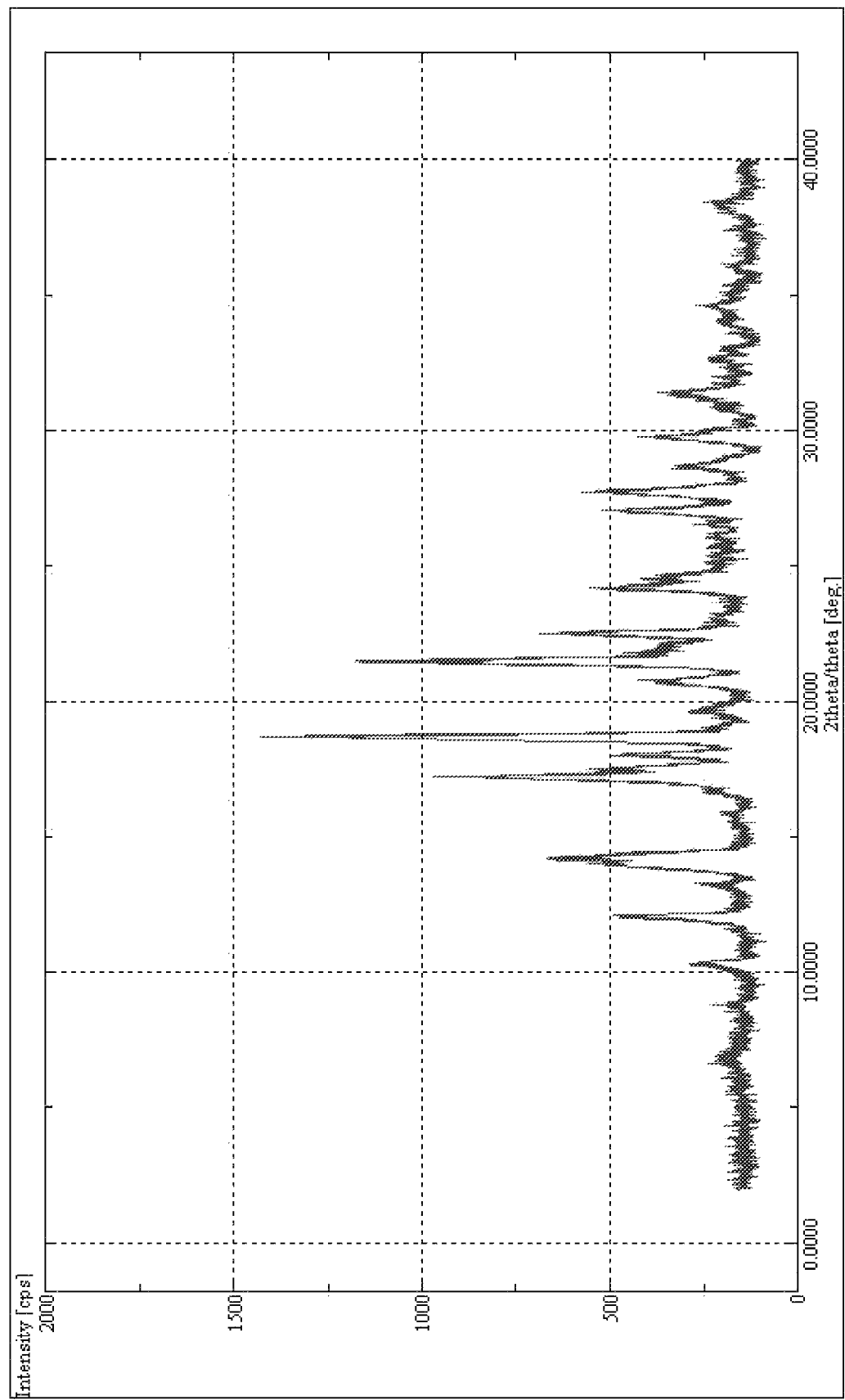
FIG. 4 shows an X-ray powder diffraction pattern (XRPD) for compound (I) as an isopropanol solvate. The x-axis shows the 2-theta value and the y-axis the counts.

Step 7, alternate 3. Preparation of compound (I). Compound (III) (15.1 g, 45.06 mmol) and compound (XI) (17.31 g, 56.32 mmol) were suspended in 2-methyltetrahydrofuran (46 ml) and heated to 80° C. To this yellow suspension was added acetic acid (12 ml, 458 mmol) and the resulting solution was heated to 92° C. for 7 hours. 2-methyltetrahydrofuran (100 ml) and water (43 ml) were added and mixture was cooled to 59° C. before adding 50% w/w sodium hydroxide (11 ml, 207 mmol), resulting in a temperature rise to 71.5° C. The temperature was adjusted to 69° C. and the aqueous phase was discarded after settling. The organic phase was washed with water (2×43 ml) and each aqueous phase was discarded after settling. 2-methyltetrahydrofuran (72 ml) was removed by distillation at atmospheric pressure and was replaced by addition of isopropyl alcohol (72 ml). A further 72 ml of solvent was removed by distillation at atmospheric pressure and replaced by isopropyl alcohol (72 ml). Seed was added to induce crystallisation and the resulting mixture was cooled to 15° C. The solid was isolated by filtration, washed twice with isopropylalcohol (32 ml) and dried under vacuum at 40° C. to yield compound (I) as a white solid (20.86 g, 87%). $^1$H NMR (400 MHz, DMSO-d$_6$) δ ppm 1.04 (d, J=6 Hz, 6H), 1.75-1.88 (m, 2H), 2.02-2.15 (m, 2H), 2.35-2.44 (m, 2H), 2.64 (d, J=4.7 Hz, 3H), 2.72-2.80 (m, 2H), 2.95 (s, 2H), 3.73-3.84 (m, 1H), 3.95 (s, 3H), 4.34 (d, J=4.2 Hz, 1H), 4.53-4.63 (m, 1H), 7.22 (s, 1H), 7.29 (dt J=1 Hz J=8 Hz, 1H), 7.51 (dt J=7 Hz, J=18 Hz, 2H), 7.71-7.77 (m, 1H), 7.82 (s, 1H), 8.37 (s, 1H), 9.57 (s, 1H). Mass Spectrum: m/z (M+H)+ 474.0. The NMR data include signals for 1 mole equivalent isopropanol present. The XRPD for this compound is shown in FIG. 4.

Example 3

Preparation of 4-(3-Chloro-2-fluoroanilino)-7-methoxy-6-{[1-(N-methylcarbamoylmethyl)piperidin-4-yl]oxy}quinazoline di-[(2E)-but-2-enedioate] (compound (I) difumarate salt)

Compound (I) difumarate salt was prepared according to the scheme shown below:

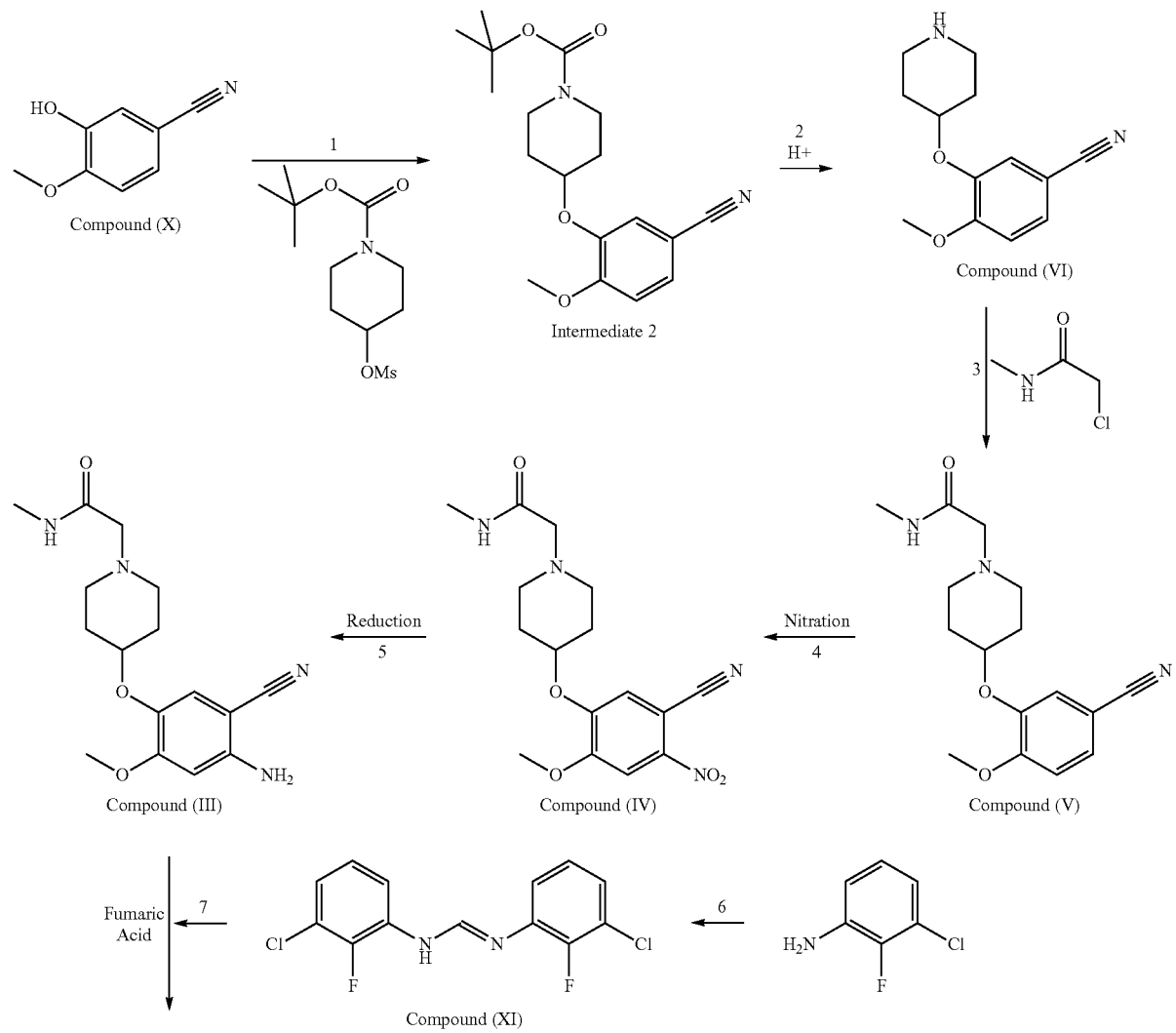

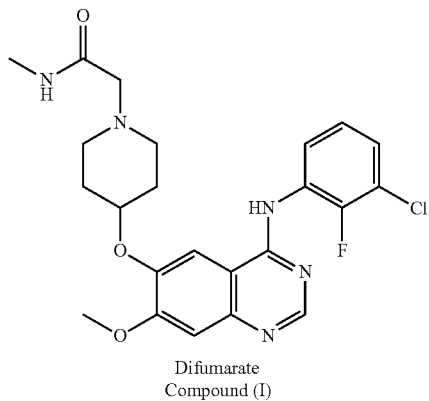
Difumarate
Compound (I)

Steps 1, 2, 3, 4, 5 and 6 were performed as set forth in Example 2.

Step 7. Preparation of compound (I) difumarate salt. Compound (III) (17.90 mmoles) and N,N'-bis(3-chloro-2-fluorophenyl)imidoformamide (compound (XI)) (7.04 g, 23.27 mmoles) were suspended in tert-butyl alcohol (88.95 g). To this suspension fumaric acid (10.39 g, 89.52 mmoles) was added and the mixture was heated to 80° C., with stirring, for 2.5 hrs. Water (11.40 g, 632.80 mmoles) was charged and the reaction continued for a further 21.5 hrs. The reaction was cooled to 20° C. over 12 hours, during which time crystallisation occurred. The resulting solid was isolated by filtration and was washed with a mixture of water (1.00) and tert-butyl alcohol (7.80 g) followed by a wash with a mixture of water (0.50 g) and tert-butyl alcohol (7.30 g). The solid was dried in vacuo at 40° C. to give compound (I) difumarate salt (8.17 g, 61.40%) as a mustard yellow powder; $^1$H NMR (400 MHz, DMSO-$d_6$) δ ppm 1.83 (m, 2H, broad) 2.07 (m, 2H, broad) 2.64 (d, J=5.0 Hz, 3H) 2.80 (m, 2H, broad) 3.03 (s, 2H) 3.94 (s, 3H) 4.58 (m, 1H) 6.63 (s, 4H) 7.22 (s, 1H) 7.29 (td, J=8.5, 1.0 Hz, 1H) 7.51 (m, 2H) 7.82 (m, 2H) 8.37 (s, 1H); Mass Spectrum: m/z (M+H)$^+$ 474.0.

Example 4

Preparation of 4-(3-Chloro-2-fluoroanilino)-7-methoxy-6-{[1-(N-methylcarbamoylmethyl)piperidin-4-yl]oxy}quinazoline di-[(2E)-but-2-enedioate] (compound (I) difumarate salt)

Compound (I) difumarate salt was prepared according to the scheme shown below:

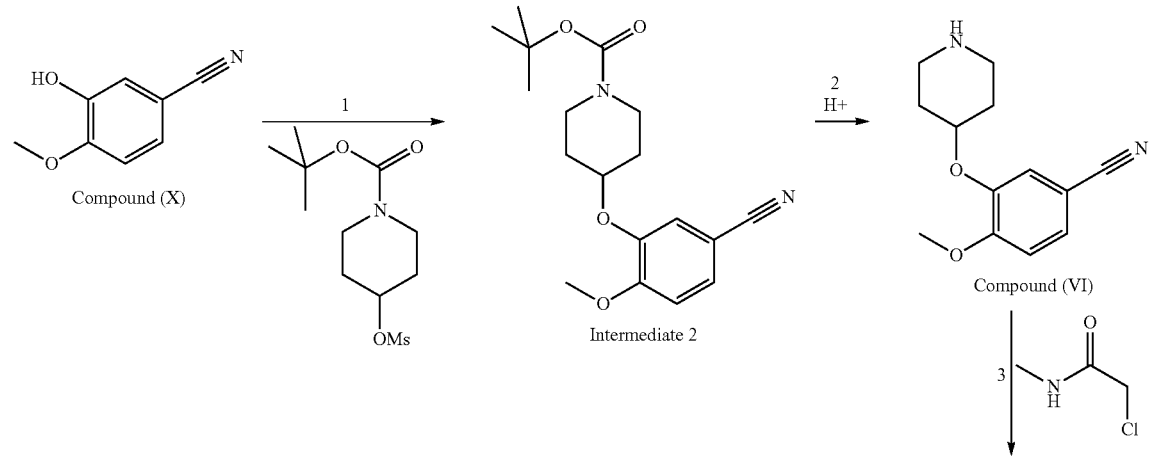

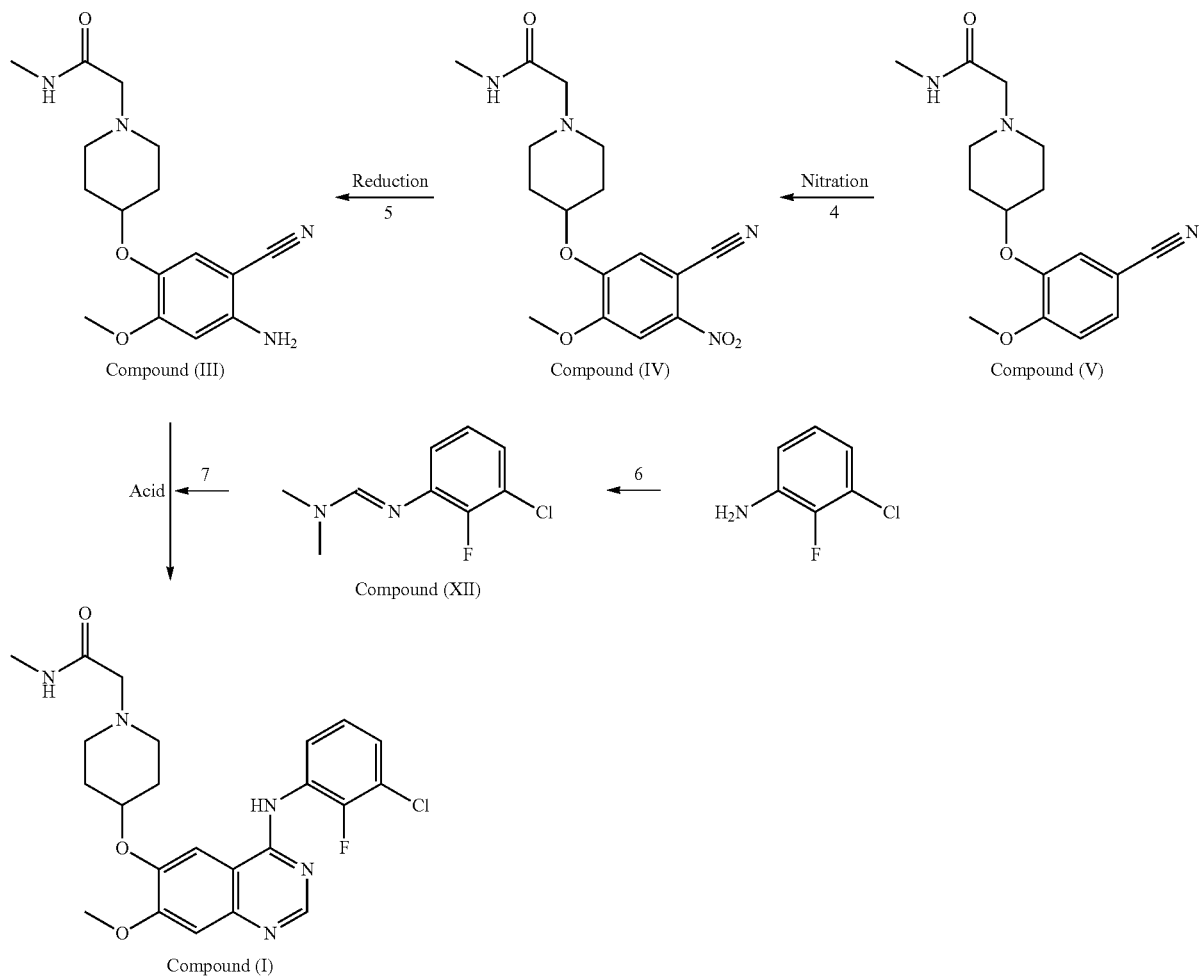

Steps 1, 2, 3, 4 and 5 were performed as set forth in Example 2.

Step 6. Preparation of N'-(3-chloro-2-fluoro-phenyl)-N,N-dimethyl-formamidine (compound (XII)). 3-chloro-2-fluoroaniline (5.30 g, 35.29 mmoles) was dissolved in 2-methyltetrahydrofuran (52.94 g). To this N,N-dimethylformamide dimethyl acetal (6.07 g, 49.41 mmoles) and acetic acid (0.11 g, 1.76 mmoles) were added. The resulting reaction mixture was heated, with stirring, to 76° C. for 3 hours. Following this the solvent was removed in vacuo at 40° C. to give compound (XII) as a yellow oil (6.60 g, 93% yield); 1H NMR Spectrum (400 MHz, DMSO-d6) δ ppm 2.74 (s, 0.29H), 2.89 (s, 0.31H), 2.94 (s, 2.75H), 3.03 (s, 2.66H), 3.34 (br s, 0.70H), 5.48 (s, 0.06H) 6.91-7.10 (m, 3H), 7.79 (s, 1H), 7.96 (s, 1H). The NMR data above includes signals for N,N-dimethylformamide dimethyl acetal which is present in a 0.06 molar equivalence. The signals pertaining to N,N-dimethylformamide dimethyl acetal are at δ ppm shifts of 3.75, and 6.90-6.95. The signal at δ ppm 3.35 is due to residual water. Mass Spectrum (by LCMS EI): m/z (M+H)⁺ 201.2.

Step 7: Preparation of compound (I). 2-[4-(4-Amino-5-cyano-2-methoxyphenoxy)piperidin-1-yl]-N-methylacetamide (compound (III)) (0.50 g, 1.45 mmol) and N'-(3-chloro-2-fluoro-phenyl)-N,N-dimethyl-formamidine (compound (XII)) (0.32 g, 1.52 mmol) were suspended in methoxybenzene (3.1 ml). To this yellow suspension was added acetic acid (1.52 ml, 25.51 mmol) and the resulting solution was heated to 90° C. for 14 hours. The reaction mixture was cooled to 20° C. and water (2.58 mL) was added. The organic layer was removed and the aqueous layer washed with methoxybenzene (1.4 mL). Ethanol (2.45 mL) and ammonia (1.94 ml, 25.55 mmoles) were added to the aqueous layer. The solution was heated to 90° C. resulting in the loss of some ethanol by evaporation. The solution was cooled to 40° C. Seed was added to induce crystallisation and the resulting mixture was cooled to 20° C. The solid was isolated by filtration to yield compound (I) as a white solid (0.61 g, 73% yield). 1H NMR (400 MHz, DMSO-d6) δ ppm 1.75-1.87 (m, 2H), 2.02-2.15 (m, 2H), 2.35-2.44 (m, 2H), 2.64 (d, J=4.8 Hz, 3H), 2.72-2.80 (m, 2H), 2.95 (s, 2H), 3.35 (s, 5.4H), 3.75 (s, 1.3H), 3.95 (s, 3H), 4.58 (hept., J=4.0 Hz, 1H), 6.90-6.95 (m, 1.3H), 7.23 (s, 1.8H), 7.26-7.34 (m, 1H), 7.45-7.58 (m 2H), 7.72-7.78 (m, 1H), 7.83 (s, 1H), 8.38 (s, 1H), 9.58 (s, 1H). The NMR data above includes signals for the methoxybenzene solvent which is present in a 0.40 molar equivalence. The signals pertaining to the solvent are at δ ppm shifts of 3.75, and 6.90-6.95. The cluster at 7.26-7.34 contains signals for the solvent and the parent compound. The signal at δ ppm 3.35 is due to residual water. Mass Spectrum: m/z (M+H)+ 474.0, 476.0.

Example 5

Preparation of compound (I) difumarate Form A-2-[4-({4-[(3-Chloro-2-fluorophenyl)amino]-7-methoxyquinazolin-6-yl}oxy)piperidin-1-yl]-N-methylacetamide di-[(2E)-but-2-enedioate] Form A A solution of fumaric acid (2.7 g, 23.22 mmol) in methanol (95 ml) was added to a mixture of 2-[4-({4-[(3-Chloro-2-fluorophenyl)amino]-7-methoxyquinazolin-6-yl}oxy)piperidin-1-yl]-N-methylacetamide (compound (I)) (5.62 g at 89% w/w, 10.55 mmol) in isopropanol (100 ml) maintaining the temperature >65° C. The mixture was heated at reflux for one hour before clarification. The reaction mixture was cooled to 30° C. over 90 minutes and held for 30 minutes to establish crystallisation. The reaction was cooled to 0° C. over 2 hours and held for 1 hour before isolation by filtration. The filter cake was washed twice with cold isopropanol (2×10 ml) and dried in vacuo at 50° C. to give the title compound as a white solid (5.84 g, 78%); $^1$H NMR Spectrum: (DMSO) 1.85 (m, 1H), 2.08 (m, 1H), 2.50 (m, 1H), 2.66 (d, 3H), 2.83 (m, 1H), 3.05 (s, 2H), 3.96 (s, 3H), 4.58 (m, 1H), 6.64 (s, 4H), 7.23 (s, 1H), 7.28 (m, 1H), 7.46 (ddd, 1H), 7.55 (m, 1H), 7.70 (broad q, 1H), 7.85 (s, 1H), 8.38 (s, 1H).

Example 6

Preparation of compound (I) difumarate Form A: 2-[4-({4-[(3-Chloro-2-fluorophenyl)amino]-7-methoxyquinazolin-6-yl}oxy)piperidin-1-yl]-N-methylacetamide di-[(2E)-but-2-enedioate] Form A A solution of fumaric acid (1.4 kg, 12.1 mol) in methanol (26.6 kg) was added to a mixture of 2-[4-({4-[(3-chloro-2-fluorophenyl)amino]-7-methoxyquinazolin-6-yl}oxy)piperidin-1-yl]-N-methylacetamide (2.93 kg, 84.8% w/w, 5.24 mol) in isopropanol (39 kg) maintaining the temperature >65° C. A line wash of methanol (3.6 kg) was charged. The mixture was heated at reflux for one hour before clarification, followed by a line wash of methanol (7 kg). The reaction mixture was distilled at atmospheric pressure to remove 47 kg of distillates. Isopropanol (15.8 kg was added and the reaction mixture distilled to remove 15.6 kg of distillates. Crystallisation occurred during the distillation. Isopropanol (21 kg) was added and the reaction cooled to 0° C. over 8 hours and held for 1 hour before isolation by filtration. The filter cake was washed with cold 50:50 isopropanol:MeOH (4 kg) followed by cold isopropanol (4 kg) and dried in vacuo at 50° C. to give the title compound as a white solid (3.64 kg, 98%); $^1$H NMR Spectrum: (DMSO) 1.85 (m, 1H), 2.08 (m, 1H), 2.50 (m, 1H), 2.66 (d, 3H), 2.83 (m, 1H), 3.05 (s, 2H), 3.96 (s, 3H), 4.58 (m, 1H), 6.64 (s, 4H), 7.23 (s, 1H), 7.28 (m, 1H), 7.46 (ddd, 1H), 7.55 (m, 1H), 7.70 (broad q, 1H), 7.85 (s, 1H), 8.38 (s, 1H).

Example 7

Preparation of compound (I) difumarate Form A: 2-[4-({4-[(3-Chloro-2-fluorophenyl)amino]-7-methoxyquinazolin-6-yl}oxy)piperidin-1-yl]-N-methylacetamide di-[(2E)-but-2-enedioate] Form A 2-[4-({4-[(3-Chloro-2-fluorophenyl)amino]-7-methoxyquinazolin-6-yl}oxy)piperidin-1-yl]-N-methylacetamide (compound (I)) (60.19 g at 88% w/w, 111.8 mmol) was dissolved in ethyl acetate (1550 ml). The solution was clarified by filtration and the filter washed with ethyl acetate (53 ml). The solution was cooled to 40° C. A clarified solution of fumaric acid (26.60 g, 257.0 mmol) in isopropanol (408 ml) was then added over 1 hour. The filter used to clarify the fumaric acid solution was then washed with isopropanol (37 ml). After holding for 1 hour at 40° C. the reaction was cooled to 20° C. over 1 hour. The reaction mixture was held for 13.5 hours before isolating the product by filtration. The filter cake was washed twice with ethyl acetate (82 ml): isopropanol (24 ml) and then dried in vacuo at 40° C. to give the title compound as a white solid (72.32 g, 90%); $^1$H NMR Spectrum: (DMSO) 1.85 (m, 1H), 2.08 (m, 1H), 2.50 (m, 1H), 2.66 (d, 3H), 2.83 (m, 1H), 3.05 (s, 2H), 3.96 (s, 3H), 4.58 (m, 1H), 6.64 (s, 4H), 7.23 (s, 1H), 7.28 (m, 1H), 7.46 (ddd, 1H), 7.55 (m, 1H), 7.70 (broad q, 1H), 7.85 (s, 1H), 8.38 (s, 1H).

Example 8

Preparation of compound (I) difumarate Form A: 2-[4-({4-[(3-Chloro-2-fluorophenyl)amino]-7-methoxyquinazolin-6-yl}oxy)piperidin-1-yl]-N-methylacetamide di-[(2E)-but-2-enedioate] Form A 2-[4-({4-[(3-Chloro-2-fluorophenyl)amino]-7-methoxyquinazolin-6-yl}oxy)piperidin-1-yl]-N-methylacetamide (compound (I)) (2.75 g at assumed 100% w/w, 5.80 mmol) was dissolved in ethyl acetate (94 ml) and isopropanol (14 ml). The solution was distilled such that 25.2 ml of distillates were collected. The solution was cooled to 40° C. A clarified solution of fumaric acid (1.38 g, 11.90 mmol) in isopropanol (21 ml) was then added over 1 hour. Compound (I) difumarate Form A seed was added (3.7 mg, 5.3 µmol). The filter used to clarify the fumaric acid solution was then washed with isopropanol (2 ml). After holding for 1 hour at 40° C. the reaction was cooled to 20° C. over 2 hours. The reaction mixture was held for 15 hours before isolating the product by filtration. The filter cake was washed twice with ethyl acetate (4.3 ml): isopropanol (1.2 ml) and then dried in vacuo at 40° C. to give the title compound as a white solid (72.32 g, 90%); $^1$H NMR Spectrum: (DMSO) 1.85 (m, 1H), 2.08 (m, 1H), 2.50 (m, 1H), 2.66 (d, 3H), 2.83 (m, 1H), 3.05 (s, 2H), 3.96 (s, 3H), 4.58 (m, 1H), 6.64 (s, 4H), 7.23 (s, 1H), 7.28 (m, 1H), 7.46 (ddd, 1H), 7.55 (m, 1H), 7.70 (broad q, 1H), 7.85 (s, 1H), 8.38 (s, 1H).

Example 9

Preparation of compound (I) difumarate Form A: 2-[4-({4-[(3-Chloro-2-fluorophenyl)amino]-7-methoxyquinazolin-6-yl}oxy)piperidin-1-yl]-N-methylacetamide di-[(2E)-but-2-enedioate] Form A 2-[4-({4-[(3-Chloro-2-fluorophenyl)amino]-7-methoxyquinazolin-6-yl}oxy)piperidin-1-yl]-N-methylacetamide (compound (I)) (1 g, 1.86 mmoles) and fumaric acid (0.44 g, 3.81 mmoles) were suspended in water (4.4 g) and heated to 85° C. The reaction mixture was cooled to 60° C. at 1° C./minute and compound (I) Form A seed was added when the temperature was 77° C. The resulting solid was isolated by filtration, washed twice with acetone (0.70 g per wash) and dried in a vacuum oven at 40° C. to afford the title compound (0.89 g, 68% yield), 1H NMR (400 MHz, DMSO-d6) d ppm 1.84 (m, 2H) 2.08 (m, 2H) 2.55 (m, 2H) 2.63 (d, J=4.7 Hz, 3H) 2.86 (m, 2H) 3.12 (s, 2H) 3.93 (s, 3H) 4.59 (tt, J=7.8, 3.7 Hz, 1H) 6.62 (s, 4H) 7.21 (s, 1H) 7.27 (td, J=8.1, 1.3 Hz, 1H) 7.49 (m, 2H) 7.86 (m, 2H) 8.36 (s, 1H) 9.63 (br. s., 1H).

Compound (I) difumarate Form A is a free flowing powder. X-ray powder diffraction of compound (I) difumarate (FIG. 1) indicates that the material is crystalline. The X-Ray Powder Diffraction analysis was carried out using a Siemens D5000 powder X-ray diffractometer fitted with a scintillation detector; the X-Ray source was Cu K$_\alpha$, giving a wavelength of 1.54 Å; data were collected over the range 2-theta 2-40°, in increments of 2-theta 0.02°, with 1 second per increment and was categorised into the categories identified in the table below:

| % Relative Intensity* | Definition |
| --- | --- |
| 25-100 | vs (very strong) |
| 10-25 | s (strong) |
| 3-10 | m (medium) |
| 1-3 | w (weak) |

*The relative intensities are derived from diffractograms measured with fixed slits.

Persons skilled in the art of X-ray powder diffraction will realise that the relative intensity of peaks can be affected by, for example, grains above 30 microns in size and non-unitary aspect ratios, which may affect analysis of samples. The skilled person will also realise that the position of reflections can be affected by the precise height at which the sample sits in the diffractometer and the zero calibration of the diffractometer. The surface planarity of the sample may also have a small effect. Hence the diffraction pattern data presented are not to be taken as absolute values (see Jenkins, R & Snyder, R. L. 'Introduction to X-Ray Powder Diffractometry' John Wiley & Sons, 1996, for further information)

Example 10

Tablet formulation of compound (I) difumarate. The powdered ingredients are charged to a mixer and mixed to produce a uniform distribution of drug substance. A binder solution is prepared and added to the powders with further mixing until a suitable wet mass is formed. The wet mass is passed through a screen and the resultant granules dried to an appropriate moisture content. The dried granules are passed through an appropriately sized screen and blended with magnesium stearate before compressing into tablet cores using conventional tabletting equipment. The compressed cores are coated with an aqueous suspension of film coating components using a conventional perforated drum coater.

Film-coated tablets containing compound (I) difumarate Form A equivalent to 2.5, 10, 40 and 100 mg of compound (I) prepared as described above are illustrated in Table 1 below:

TABLE 1

| | Tablet strength[1] | | | |
| --- | --- | --- | --- | --- |
| Ingredient | 2.5 mg g/batch | 10 mg g/batch | 40 mg g/batch | 100 mg g/batch |
| Tablet core | | | | |
| Compound (I) Difumarate Form A[2] | 37.25 | 149.0 | 448.1 | 448.1 |
| Lactose (450 mesh) | 782.75 | 671.0 | 371.9 | 371.9 |
| Microcrystalline cellulose (PH101) | 100.0 | 100.0 | 100.0 | 100.0 |
| Crospovidone | 50.0 | 50.0 | 50.0 | 50.0 |
| Polyvidone | 20.0 | 20.0 | 20.0 | 20.0 |
| Magnesium stearate | 10.0 | 10.0 | 10.0 | 10.0 |
| Core tablet weight | 100 mg | 100 mg | 133 mg | 333 mg |
| Tablet coating | | | | |
| Opadry White (03B28460) | 23.0 | 23.0 | 23.3 | 23.0 |
| Hypromellose[3] | 15.0 | 15.0 | 15.0 | 15.0 |

TABLE 1-continued

| | Tablet strength[1] | | | |
| --- | --- | --- | --- | --- |
| Ingredient | 2.5 mg g/batch | 10 mg g/batch | 40 mg g/batch | 100 mg g/batch |
| Titanium dioxide[3] | 5.0 | 5.0 | 5.3 | 5.0 |
| Macrogol 300[3] | 3.0 | 3.0 | 3.0 | 3.0 |
| Purified water[4] | 177.0 | 177.0 | 176.7 | 177.0 |
| Nominal coated tablet weight | 102.1 mg | 102.1 mg | 136.1 mg | 140.6 mg |

[1]Tablet strengths refer to the equivalent amount of compound (I) free base present in the tablet.
[2]The compound (I) difumarate was micronised prior to formulation to give an average particle size of less than about 5 µm.
[3]The hypromellose, macrogol 300 and titanium dioxide are included as Opadry White (03B28460), supplied by Colorcon.
[4]Purified water is used as the solvent/carrier fluid during film-coating and is removed during the coating process.

Figure 5:
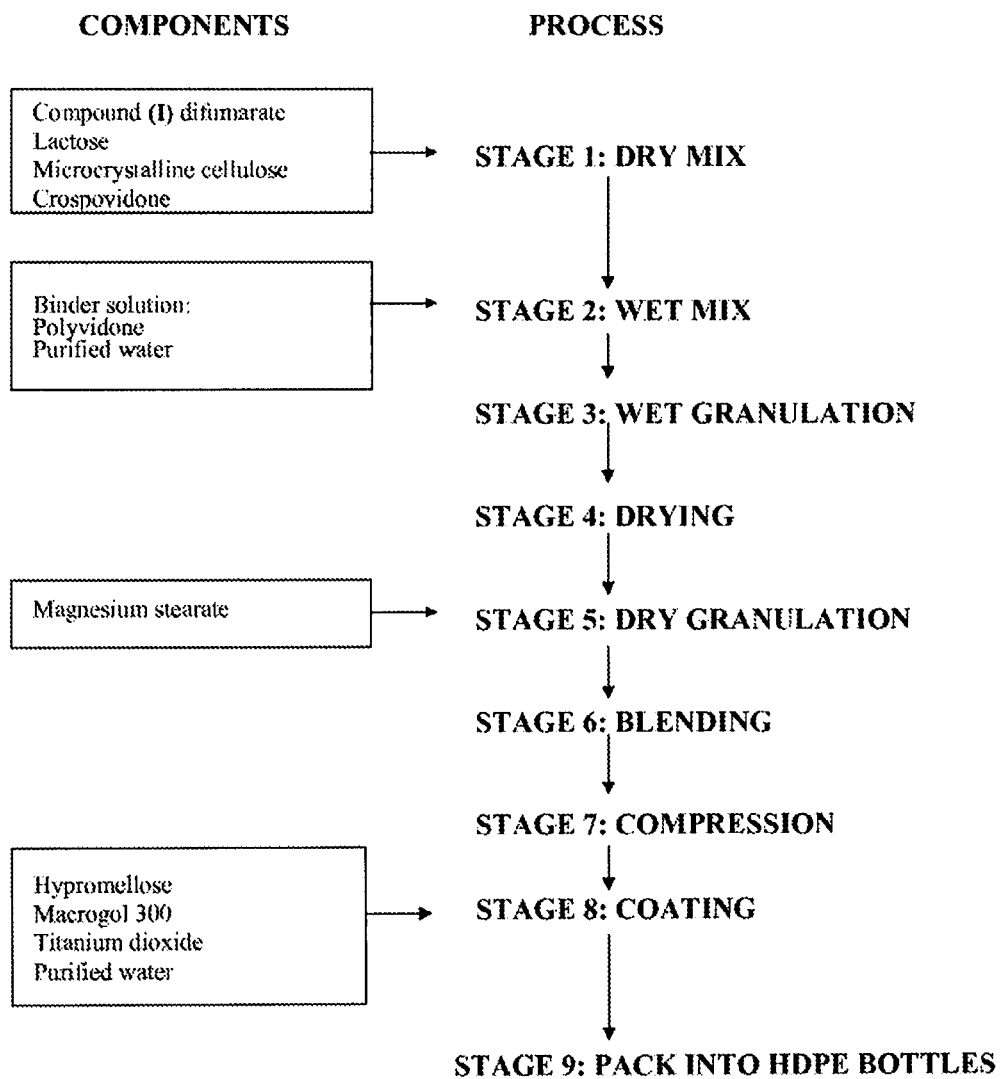
FIG. 5 shows a suitable manufacturing process for tablets exemplified in Example 10.

A suitable manufacturing process for the preparation of the tablets is shown in FIG. 5.

Those skilled in the art recognize that the compounds described herein can occur in the free, non-salt, form or can occur as salts, and the use of the term "compound" encompasses free forms of the compounds as well as salts of the compounds.

As will be understood by one skilled in the art, for any and all purposes, particularly in terms of providing a written description, all ranges disclosed herein also encompass any and all possible subranges and combinations of subranges thereof as well as the individual values making up the range, particularly integer values. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Additionally, for all purposes, the present invention encompasses not only the main group, but also the main group absent one or more of the group members. The present invention also envisages the explicit exclusion of one or more of any of the group members in the claimed invention.

As will be understood by the skilled artisan, all numbers, including those expressing quantities of ingredients, properties such as molecular weight, reaction conditions, and so forth, is are approximations and understood as being modified in all instances by the term "about." These values can vary depending upon the desired properties sought to be obtained by those skilled in the art utilizing the present teachings of the present invention. It is also understood that such values inherently contain variability necessarily resulting from the standard deviations found in their respective testing measurements.

All references disclosed herein are specifically incorporated herein by reference thereto.

Reference to a "step" in the application, or the numbering for a "step", is used for convenience purposes only and does not categorize, define or limit the invention as set forth herein.

While specific embodiments have been illustrated and described, it should be understood that these embodiments do not limit the scope of the invention and that changes and modifications can be made in accordance with ordinary skill in the art without departing from the invention in its broader aspects as defined in the following claims.

What is claimed is:

1. A process for the preparation of 4-(3-chloro-2-fluoroanilino)-7-methoxy-6-{[1-(N-methylcarbamoylmethyl)piperidin-4-yl]oxy}quinazoline or a salt thereof comprising:

(a) the reaction of a compound of formula (II):

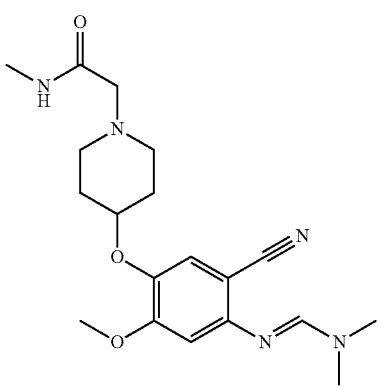

II with 3-chloro-2-fluoroaniline in the presence of a suitable acid; or (b) the reaction of a compound of formula (III):

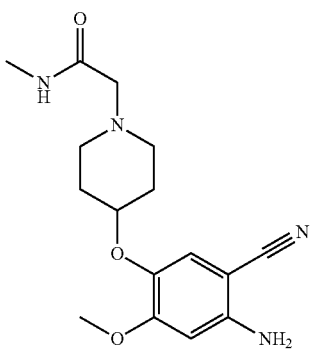

III with a compound of formula (XI) or formula (XII):

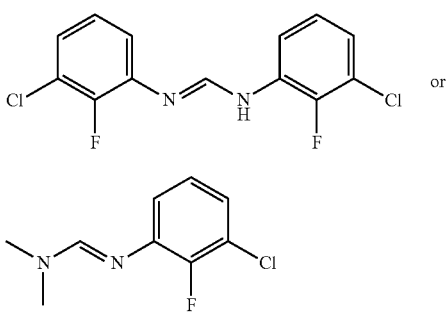

XI or

XII in the presence of a suitable acid.

2. The process according to claim 1 wherein the acid is acetic acid, butanedioic acid, fumaric acid or propanoic acid.

3. The process according to claim 1 wherein the compound of formula (II) is prepared by a process comprising reacting a compound of formula (III):

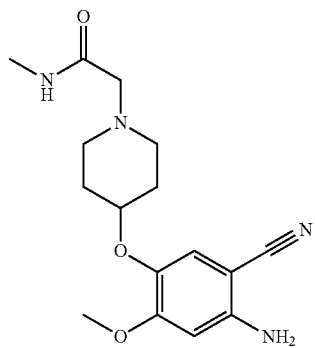

III with N,N-dimethylformamide dimethyl acetal.

4. The process according to claim 1 wherein the compound of formula (III) is prepared by a process comprising the reduction of a compound of formula (IV):

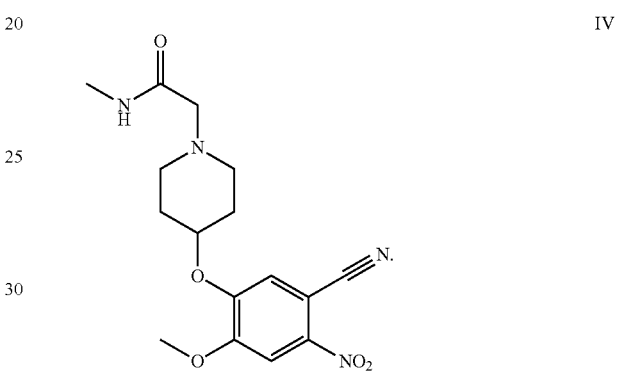

IV

5. The process according to claim 4 wherein the compound of formula (IV) is prepared by a process comprising the nitration of a compound of formula (V):

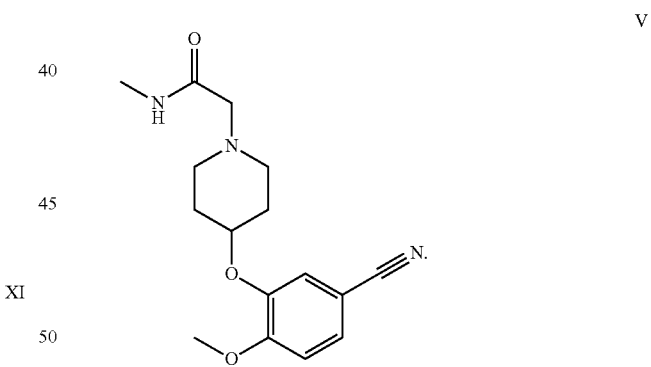

V

6. The process according to claim 5 wherein the compound of formula (V) is prepared by a process comprising the reaction of a compound of formula (VI):

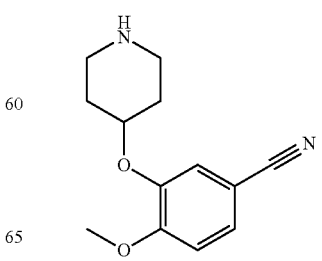

VI with a compound of formula (VII):

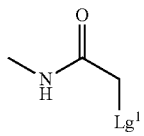

VII wherein Lg¹ is a suitable leaving group.

7. The process according to claim 6 wherein the compound of formula (VI) is prepared by a process comprising the deprotection of a compound of formula (VIII):

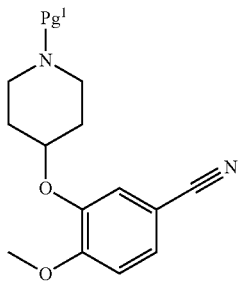

VIII wherein Pg¹ is a suitable amino protecting group.

8. The process according to claim 7 wherein the compound of formula (VIII) is prepared by a process comprising the reaction of a compound of formula (X):

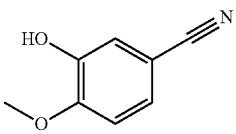

X with a compound of formula (IX):

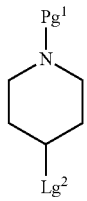

IX wherein Lg² is a suitable leaving group; and
Pg¹ is a suitable amino protecting group.

* * * * *